(12) United States Patent
Rao et al.

(10) Patent No.: US 8,034,622 B2
(45) Date of Patent: Oct. 11, 2011

(54) SELECTIVE DETECTION OF HG2+ BY CALIX[4]ARENES

(75) Inventors: Chebrolu Pulla Rao, Mumbai (IN); Roymon Joseph, Mumbai (IN)

(73) Assignee: Indian Institute of Technology Bombay, Mumbai (IN)

( * ) Notice: Subject to any disclaimer, the term of this patent is extended or adjusted under 35 U.S.C. 154(b) by 60 days.

(21) Appl. No.: 12/623,956

(22) Filed: Nov. 23, 2009

(65) Prior Publication Data
US 2010/0330681 A1 Dec. 30, 2010

Related U.S. Application Data

(60) Provisional application No. 61/221,924, filed on Jun. 30, 2009.

(51) Int. Cl.
*G01N 33/20* (2006.01)
*C07D 403/02* (2006.01)
*C07F 3/12* (2006.01)

(52) U.S. Cl. .................. 436/81; 548/108; 548/305.4

(58) Field of Classification Search .............. 436/81, 436/91, 106, 115, 164; 548/305.4, 108
See application file for complete search history.

(56) References Cited

OTHER PUBLICATIONS

Gutsche, C. D. et al., "Calixarenes. 4. The Synthesis, Characterization, and Properties of the Calixarenes from *p-tert*-Butylphenol," J. Am. Chem. Soc., vol. 103, 1981, pp. 3782-3792.
Joseph, R. et al., "Experimental and Computational Studies of Selective Recognition of $Hg^{2+}$ by Amide Linked Lower Rim 1,3-Dibenzimidazole Derivative of Calix[4]arene: Species Characterization in Solution and that in the Isolated Complex, Including the Delineation of the Nanostructures," J. Org. Chem., vol. 73, 2008, pp. 5745-5758.

*Primary Examiner* — Robert J Hill, Jr.
*Assistant Examiner* — Dwan A Gerido
(74) *Attorney, Agent, or Firm* — Foley & Lardner LLP

(57) ABSTRACT

Provided herein are compounds, methods of making the compounds and methods for the sensitive and selective detection of $Hg^{2+}$ with the compounds, which are calix[4]arenes. In particular, compounds of Formula I, wherein the variables have the values described herein, may be added to a sample to be tested for $Hg^{2+}$. The compound of

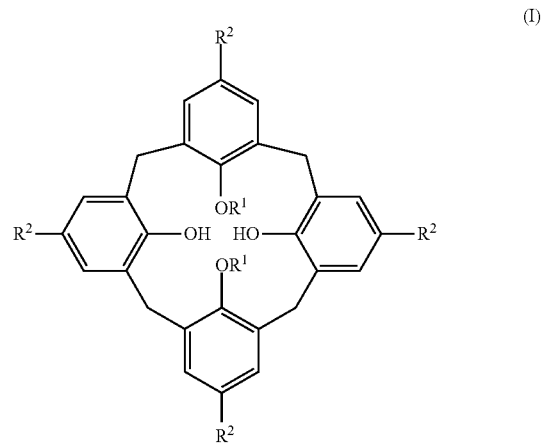

Formula (I) fluoresces strongly in the absence of $Hg^{2+}$ but is quenched upon binding of $Hg^{2+}$ to form a complex. The decrease in fluorescence may be used to detect and quantify the amount of $Hg^{2+}$ present in a sample. The disclosed compounds may also be used to selectively detect $Hg^{2+}$ in samples containing other mono- or divalent metals.

20 Claims, 12 Drawing Sheets

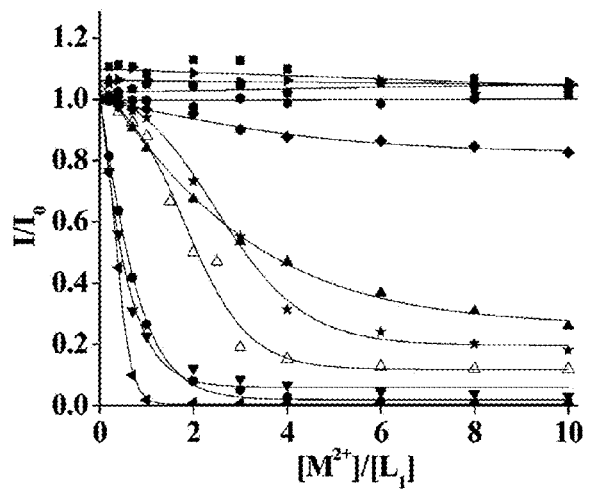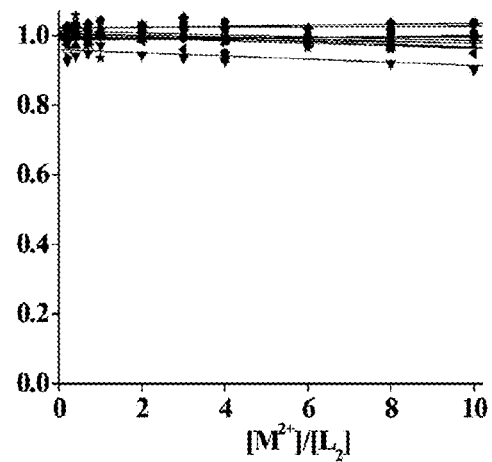
FIG. 11a  FIG. 11b
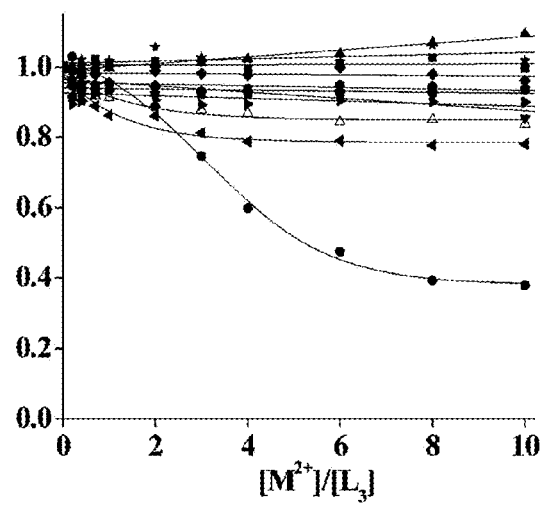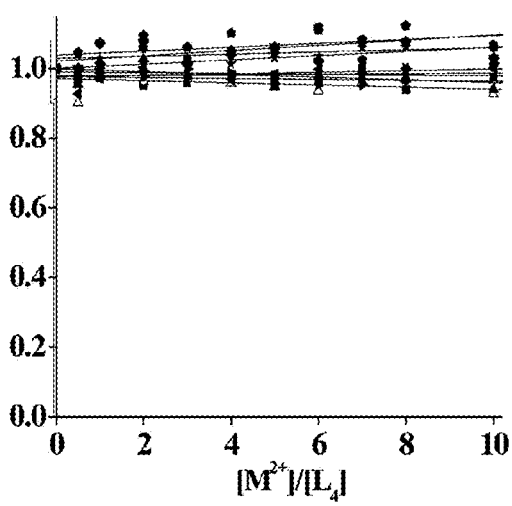
FIG. 11c  FIG. 11d

SELECTIVE DETECTION OF HG2+ BY CALIX[4]ARENES

CROSS-REFERENCE TO RELATED APPLICATION

The present application claims priority to U.S. Provisional Application No. 61/221,924, filed Jun. 30, 2009, the entire contents of which are incorporated by reference herein for any and all purposes.

BACKGROUND

Mercury is a metal which has commanded a lot of attention in the scientific world, primarily because of its toxicity. Mercury exposure can cause developmental toxicity, reproductive toxicity, chronic toxicity, acute toxicity, neurotoxicity and environmental toxicity. Acute and chronic mercury affects the kidneys, liver, gastrointestinal system and nervous system.

The sources of the mercury are commercial products such as batteries, thermometers, electrical switches, barometers, dental fillings, fluorescent light bulbs, and some blood pressure devices. Mercury can be released into the atmosphere during various manufacturing and disposal processes, or through natural water flowing over mercury deposits such as cinnabar.

Estimates of the minimal risk levels of mercury range from 0.002-0.007 mg/kg/for oral exposure and 0.0002 mg/m$^3$ for inhalation. The most harmful form of mercury is ionic mercury, which appears as $Hg^{2+}$, a doubly charged positive ion. A small amount of the ion, $Hg_2^{2+}$ may also be present in some cases, but it quickly decomposes to metallic mercury and the ion $Hg^{2+}$. Thus, methods for assessing low levels of mercury in both biological and other sample types would be useful.

SUMMARY

The present technology provides compounds and simple, sensitive and accurate methods using the compounds to detect mercury in various test samples.

Accordingly, in one aspect, there are provided compounds having Formula I:

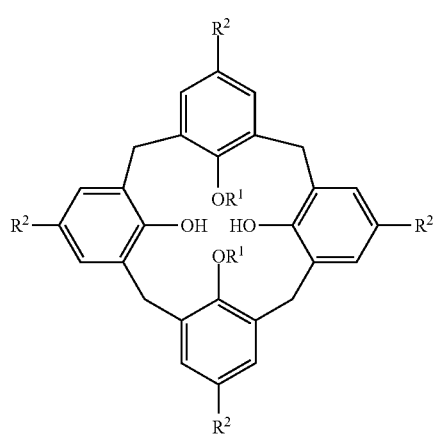

(I)

or salts thereof, wherein
each $R^1$ is

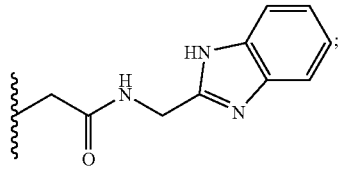

and
each $R^2$ is independently a $C^{3-6}$ straight, branched or cyclic alkyl group.

In some embodiments of the compounds, each $R^2$ is a isopropyl, t-butyl, cyclopropyl, cyclobutyl, cyclopentyl or cyclohexyl group. In some embodiments, each $R^2$ is a t-butyl group and the compound is referred to herein as "L".

In another aspect, there are provided complexes including a compound as disclosed herein (e.g., compounds of Formula I) and a $Hg^{2+}$ ion. In some embodiments, there is provided a complex including the compound L and a $Hg^{2+}$ ion.

In another aspect, there are provided methods of testing for the presence of $Hg^{2+}$. The method includes detecting the fluorescence of a test sample including a compound of Formula I, and comparing the detected fluorescence of the test sample to that of a control sample, wherein a reduction in fluorescence of the test sample relative to the control sample indicates the presence of $Hg^{2+}$ in the sample. In some embodiments, the method further includes combining a compound of Formula I with the test sample prior to detecting the fluorescence of the test sample. In some embodiments, the control sample contains substantially the same amount of compound as the test sample but lacks $Hg^{2+}$. In some embodiments, the compound of Formula I is compound L.

In other embodiments, the methods include: preparing a test sample including the compound L; detecting the fluorescence of the test sample; and comparing the detected fluorescence of the test sample to that of a control sample, wherein a reduction in fluorescence of the test sample relative to the control sample indicates the presence of $Hg^{2+}$ in the test sample.

In some embodiments of the methods, the test sample is an aqueous solution. In some embodiments, the aqueous solution includes about 10 to about 90% acetonitrile. In some embodiments, the aqueous solution includes about 40 to about 75% acetonitrile. In still other embodiments, the aqueous solution includes about 50% acetonitrile. In other embodiments the control sample is an aqueous solution.

In some embodiments of the methods, the method selectively detects the presence of $Hg^{2+}$ in the presence of one or more different divalent metal ions in the sample. In some embodiments, the one or more different divalent metal ions are selected from the group consisting of $Ca^{2+}$, $Cd^{2+}$, $Co^{2+}$, $Cu^{2+}$, $Fe^{2+}$, $Mg^{2+}$, $Mn^{2+}$, $Ni^{2+}$, $Pb^{2+}$, and $Zn^{2+}$.

In another aspect, there are provided methods for preparing a compound of Formula I including contacting 2-aminomethyl benzimidazole in the presence of a suitable base with a compound of Formula II:

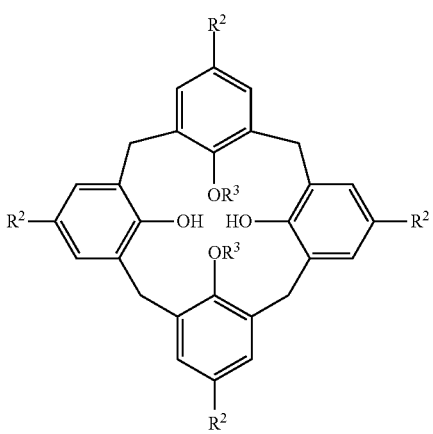

(II)

wherein R³ is —CH₂COX and X is a halide.

In some embodiments, the suitable base is a tertiary amine or a pyridine compound. In some embodiments, the suitable base is selected from the group consisting of triethylamine, diisopropylethylamine, pyridine, and dimethylaminopyridine.

In another aspect, there are provided methods for preparing a compound of Formula I including activating carboxyl groups of Formula II for amide bond formation and reacting the activated compound of Formula II with 2-aminomethyl benzimidazole to give the compound of Formula I, wherein the compound of Formula II is:

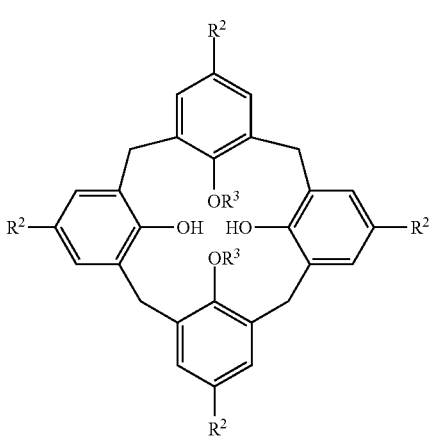

(II)

wherein R³ is —CH₂COOH.

In some embodiments, the compound of Formula II is activated by forming an halide from each R³ group. In some embodiments, the compound of Formula II is activated by forming an active ester, a mixed anhydride or by use of a peptide coupling reagent.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 11 depicts an illustrative embodiment of plots of $(I/I_o)$ as a function of metal to the ligand mole ratio during the fluorescence titration for reference compounds in 50% aqueous acetonitrile solution except for (b) which is in 25% aqueous acetonitrile solution: (a) $L_1$, (b) $L_2$, (c) $L_3$, and (d) $L_4$. The symbols correspond to, ■=$Mn^{2+}$; =$Fe^{2+}$; ▲=$Co^{2+}$; ▼=$Ni^{2+}$; ◄=$Cu^{2+}$; ►=$Zn^{2+}$; ◆=$Cd^{2+}$; pentagon ◆=$Ca^{2+}$; ●=$Mg^{2+}$; ★=$Pb^{2+}$; and ●=$Hg^{2+}$.

DETAILED DESCRIPTION

Figure 1:
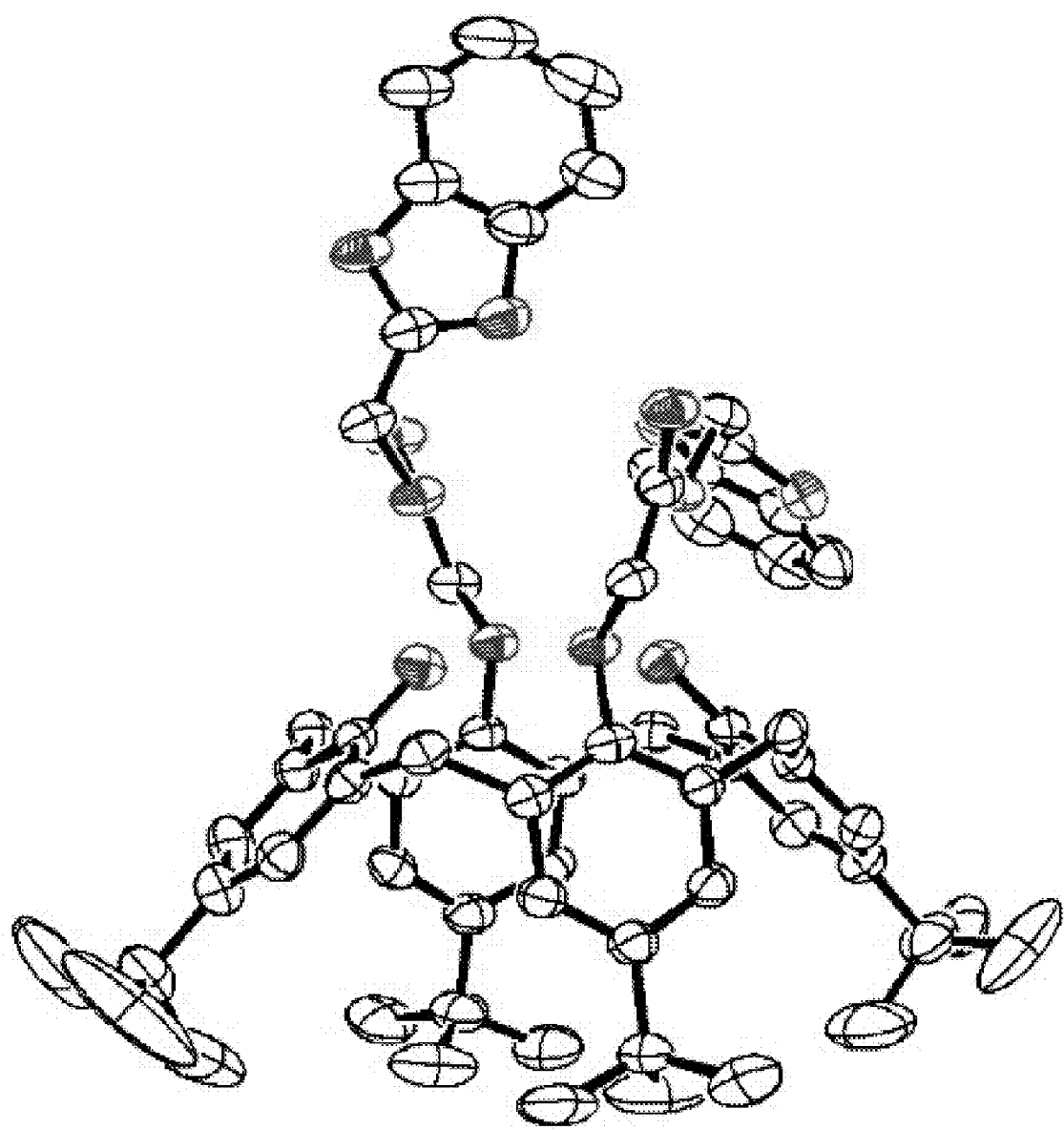
FIG. 1 depicts an illustrative embodiment of an ORTEP (Oak Ridge Thermal Ellipsoid Program) diagram of 2-aminomethyl benzimidazole derivative of calix[4]arene (compound L). Hydrogen and solvent molecules are not shown for clarity.
Figure 2A:
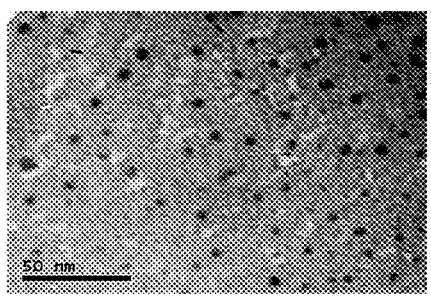
FIG. 2 depicts an illustrative embodiment of micrographs of 2-aminomethyl benzimidazole derivative of calix[4]arene (compound L) and its complex with $Hg^{2+}$ (a) TEM (transmission electron microscopy) for L in ethanol (b) TEM for mercury complex of L in ethanol (c) AFM (atomic force microscopy) for L in ethanol (d) SEM (scanning electron microscopy) for L; and (e) SEM for mercury complex of L.
Figure 2B:
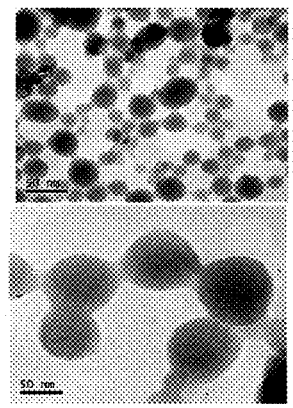
Figure 2C:
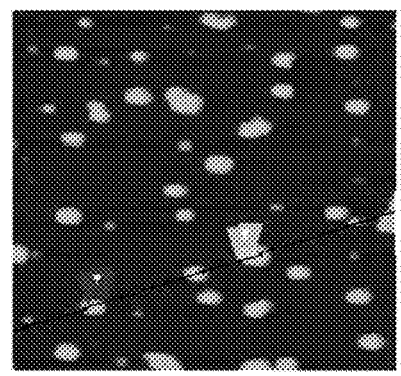
Figure 2D:
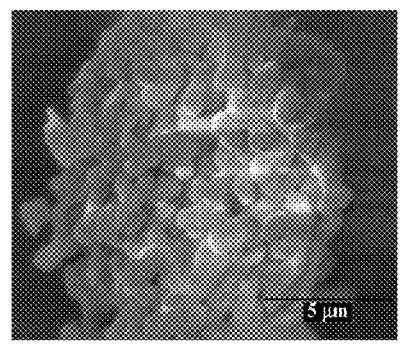
Figure 2E:
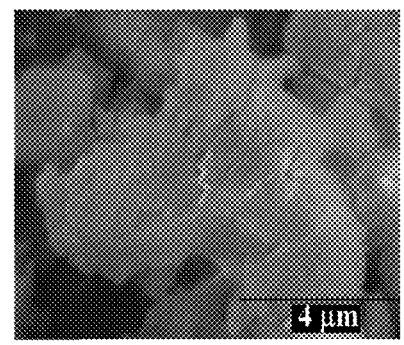

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. The present technology is also illustrated by the examples herein, which should not be construed as limiting in any way.

1. DEFINITIONS

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups.

The terms "cyclic alkyl" or "cycloalkyl" refers to a saturated or partially saturated non-aromatic cyclic alkyl groups of from 3 to 14 carbon atoms and no ring heteroatoms and having a single ring or multiple rings including fused and bridged ring systems. Cycloalkyl or cyclic alkyl groups include mono-, bi- or tricyclic alkyl groups having from 3 to 14 carbon atoms in the ring(s), or, in some embodiments, 3 to 12, 3 to 10, 3 to 8, or 3 to 4, 5, 6 or 7 carbon atoms. Exemplary monocyclic cycloalkyl groups include, but not limited to, cyclopropyl, cyclobutyl, cyclopentyl, cyclohexyl, cycloheptyl, and cyclooctyl groups. Bi- and tricyclic ring systems include both bridged cycloalkyl groups and fused rings, such as, but not limited to, bicyclo[2.1.1]hexane, adamantyl, decalinyl, and the like.

The term "base" refers to a chemical compound that can donate a pair of electrons or donate a hydroxide ion and that can deprotonate another compound when reacted with it. Examples of base include, but are not limited to, tertiary amines, pyridine compounds, sodium and potassium hydroxides, sodium and potassium carbonates, sodium and potassium hydrides, sodium and potassium alkoxides, and the like.

The term "control sample" refers to a sample against which the test sample is compared in order to assess the presence, absence and/or level of analyte in the test sample. As such, in the present methods the control sample may include some or all of the constituents of the test sample, except for the analyte being assessed, e.g., $Hg^{2+}$ ions, or some fixed amount of the analyte. It is within the skill in the art to select the proper control sample for the application at hand based on the present disclosure and knowledge in the art. Depending on the detection method being used, the control sample can be a solid sample or a liquid sample. In some embodiments, the control sample is a liquid.

In a negative control sample, the analyte being assessed, e.g. $Hg^{2+}$ ions, is completely absent. In positive control samples, such as those used for standardization, the sample may contain a known amount of the analyte being assessed.

For comparative measurement of sample fluorescence, the control sample may be dissolved in the same or substantially the same solvent/media as that of the test solvent. By "substantially the same solvent/media" is meant almost but not completely the same solvent/media.

The term "divalent metal ion" refers to any metal ion with a valency of 2. Examples of divalent ions include, but are not limited to, $Hg^{2+}$, $Ca^{2+}$, $Cd^{2+}$, $Co^{2+}$, $Cu^{2+}$, $Fe^{2+}$, $Mg^{2+}$, $Mn^{2+}$, $Ni^{2+}$, $Pb^{2+}$, and $Zn^{2+}$, and the like.

The term "halide" refers to chloro, bromo, fluoro, and iodo.

The term "solvent," as used herein, means a liquid in which a compound is soluble or partially soluble at a given concentration so as to dissolve or partially dissolve the compound. Examples of solvents include, but are not limited to, methanol, ethanol, and acetonitrile. Aqueous solutions of water-soluble solvents may also be used as solvents, e.g., aqueous solutions of methanol, ethanol or acetonitrile.

The term "tertiary amine" refers to a tri-substituted organoamine. Examples of tertiary amines include, but are not limited to, triethylamine, diisopropylethylamine, and the like.

The term "test sample" refers to any sample which is to be tested for the presence and/or concentration of an analyte, such as $Hg^{2+}$ ions. Depending on the detection method being used, the test sample can be a solid sample or a liquid sample. In some embodiments, the test sample is a liquid.

Compounds of the present technology may form salts with inorganic or organic acids. Thus, salts of the present compounds, include but are not limited to, salts of $HClO_4$, HCl, $H_2SO_4$, and $H_3PO_4$, as well as acetic acid or trifluoroacetic acid. Suitable salts include those described in P. Heinrich Stahl, Camille G. Wermuth (Eds.), Handbook of Pharmaceutical Salts Properties, Selection, and Use; 2002.

2. COMPOUNDS

In one aspect of the present technology, there is provided a calix[4]arene compound having at least 2-aminomethyl benzimidazole groups on the lower rim. The calix[4]arene compounds of the present technology detect mercury ions by a change in their fluorescence emission in solution. Binding of mercury to such calix[4]arene compounds results in a decrease in the fluorescence emission (quenching) of the compounds. It has been found that calix[4]arene compounds containing at least two 2-aminomethyl benzimidazole groups act as selective sensors for mercury ions.

Accordingly, in some embodiments of the present technology there is provided a compound of Formula I:

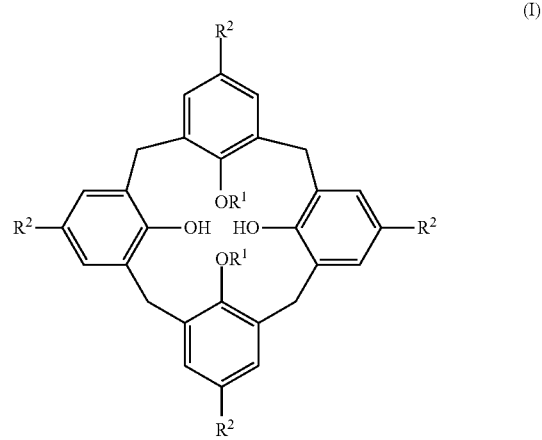

(I)

or salts thereof, wherein
each $R^1$ is

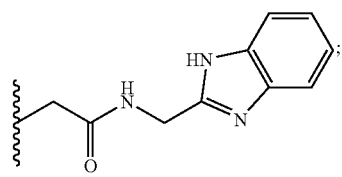

and
each $R^2$ is independently a $C_{3-6}$ straight, branched or cyclic alkyl group.

In some embodiments of the compound of Formula I, each $R^2$ is a methyl, ethyl, isopropyl, n-butyl, t-butyl, cyclopropyl, cyclobutyl, cyclopentyl or cyclohexyl group. In some embodiments, each $R^2$ is a t-butyl group and the compound is referred to herein as "L".

In another aspect, there are provided complexes including a compound as disclosed herein (e.g., compounds of Formula I) and a $Hg^{2+}$ ion. In some embodiments, the complex includes the compound L and a $Hg^{2+}$ ion. In some embodiments, the complex is a 1:1 complex between a compound of Formula I (including, e.g., the compound L) and a $Hg^{2+}$ ion.

3. METHOD OF USE

In another aspect of the present technology, there are provided methods of testing for the presence of $Hg^{2+}$ ions in a sample using the calix[4]arenes disclosed herein. In some embodiments, the methods include: detecting the fluorescence of a test sample including a compound of Formula I; and comparing the detected fluorescence of the test sample to that of a control sample, wherein a reduction in fluorescence of the sample relative to the control sample indicates the presence of $Hg^{2+}$ in the test sample. In some embodiments of the methods, the compound of Formula I is L (i.e., $R^2$ is a t-butyl group).

The methods of the present technology can be used to detect the presence of low levels of $Hg^{2+}$ ions in any test sample. In some embodiments, the test sample is a biological sample including, but not limited to, blood, cells, tissue, saliva, sweat, extracts of any of the foregoing, and the like. In some embodiments, the test sample is a nutritional sample including, but not limited to, a drink, food (including but not limited to fish and other animals eaten by humans), and extracts thereof. In some embodiments, the test sample is an environmental sample including, but not limited to, water (including surface water or underground water), and extracts and filtrates of air, soil, sediment, clay, and the like. In some embodiments, the test sample is taken from or prepared from a building where people live or work, including paint or other surface coatings, floors, walls, ceilings, furniture, toys, appliances, plumbing and plumbing fixtures (including water from water storage tanks or water heaters), and the like. Test samples may also be prepared from the aforementioned sources by use of standard techniques such as acid digestion and extraction to isolate in whole or part, the mercury to be analyzed from the rest of the sample source.

In some embodiments, the present methods include preparing the test samples by, e.g., combining a compound of Formula I, with the test sample prior to detecting the fluorescence of the sample. The compound of Formula I and the test sample may be combined in several ways. In some embodiments, the compound of Formula I may be added to the test sample as a solid or as a solution (e.g., in an organic solvent such as chloroform or acetonitrile or methanol, or aqueous organic solutions such as aqueous methanol or aqueous acetonitrile). Alternatively, the test sample or an aliquot thereof may be added to the compound of Formula I or to a solution thereof. The test sample may also be prepared by adding the compound of Formula I or a solution thereof and an aliquot of the sample to be tested to a third solution.

In some embodiments of the present methods, the compound of Formula I and the test sample can both be dissolved in the same solvent or different solvents prior to the fluorescence studies. In some embodiments, the compound of Formula I and the test sample can be dissolved in solvents such as water, alcohol, acetonitrile and the like or combinations thereof. In some embodiments, the test sample and/or the control sample is an aqueous solution. In some embodiments, the test sample may be prepared by dissolving the sample to be analyzed in an aqueous solution including water in combination with water-miscible solvents. In some embodiments, the sample to be analyzed is dissolved in an aqueous solution including water with acetonitrile or methanol. In some embodiments, the sample to be analyzed is dissolved in an aqueous acetonitrile solution. In some embodiments, the aqueous sample solution includes about 10 to 90% acetonitrile (by volume). In other embodiments, the aqueous sample solution includes about 40 to 75% acetonitrile (by volume) or about 50% acetonitrile (by volume).

In some embodiments, the test sample and the control sample are aqueous acetonitrile solutions. In some embodiments, the test sample and/or the control sample is an aqueous acetonitrile solution with about a 1:1 volume ratio of water to acetonitrile. In other embodiments, the test sample and/or the control sample is an aqueous acetonitrile solution with about a 1:3 volume ratio of water to acetonitrile. In yet other embodiments, the test sample and/or the control sample is an aqueous acetonitrile solution with about a 3:2 volume ratio of water to acetonitrile.

In some embodiments, such as those in which the amount of $Hg^{2+}$ ions are to be quantified, the methods further include comparing the detected fluorescence of the test sample with the fluorescence of a control sample, wherein a decrease in the fluorescence of the test sample relative to the control sample indicates the presence of $Hg^{2+}$ in the test sample. In some embodiments of the present methods, the control sample includes substantially the same amount of compound of Formula I as the test sample but lacks $Hg^{2+}$ ions. By "substantially the same amount of compound" in the present context is meant an amount of compound that is the same or sufficiently similar to the amount used in the test sample to allow measurement of the change in fluorescence due primarily to the binding of the $Hg^{2+}$ ions. It is to be understood that a standard concentration curve may be constructed by measuring the fluorescence of known amounts of $Hg^{2+}$ ions in the presence of the same amount of a compound of Formula I. Measurement of the fluorescence of the compound of Formula I in a test sample having an unknown amount of $Hg^{2+}$ ions, and comparison to such a standard concentration curve allows for quantification of the $Hg^{2+}$ ions.

The present methods show good to excellent sensitivity in the detection of $Hg^{2+}$ ions. While not wishing to be bound by theory, the sensitivity may result from the fact that compounds of Formula I form a 1:1 complex with $Hg^{2+}$ ions. Thus, by use of near stoichiometric amounts of the compounds in comparison to $Hg^{2+}$ ions in the sample, relatively large changes in fluorescence may be observed at low mercury concentrations. However, it is not necessary to have stoichiometric amounts of compounds of Formula I and $Hg^{2+}$ ions. The present methods can detect the presence of $Hg^{2+}$ when present in excess or in substoichiometric amounts in comparison to the amount of the compound of Formula I in the sample. In some embodiments, the present methods can be used to detect $Hg^{2+}$ in the presence of up to about 2, up to about 3, up to about 4 and up to about 5 molar equivalents of $Hg^{2+}$ in comparison to the molar amount of a compound of Formula I in a sample. In some embodiments, the present method can be used to detect $Hg^{2+}$ with a minimum concentration of about 1.4 ppm. In some embodiments, the concentration of $Hg^{2+}$ ion that can be detected in the test sample is at least about 1.3 ppm; or at least about 1.4 ppm; or at least about 1.5 ppm; or at least about 2.0 ppm; or at least about 3.0 ppm; or at least about 4.0 ppm, or at least about 5.0 ppm in the test sample. In some embodiments, the concentration of $Hg^{2+}$ ion that can be detected is in the range of about 1 ppm to about 500 ppm; or about 1.4 ppm to about 400 ppm; or about 2.0 ppm to about 300.0 ppm; or about 3.0 ppm to about 200 ppm; or about 4.0 ppm to about 100 ppm.

The present methods may also be used to selectively detect $Hg^{2+}$ ion in the presence of one or more different mono- or divalent metal ions. In some embodiments, the methods selectively detect the presence of $Hg^{2+}$ ion in the presence of one or more different monovalent metal ions, including but not limited to monovalent metal ions selected from $Li^+$, $Na^+$, and $K^+$. In some embodiments, the methods selectively detect the presence of $Hg^{2+}$ ion in the presence of one or more different divalent metal ions, including but not limited to divalent metal ions selected from $Ca^{2+}$, $Cd^{2+}$, $Co^{2+}$, $Cu^{2+}$, $Fe^{2+}$, $Mg^{2+}$, $Mn^{2+}$, $Ni^{2+}$, $Pb^{2+}$, and $Zn^{2+}$. In the presence of $Hg^{2+}$ ions, significant quenching of the fluorescence emission by the compound of Formula I is observed. In contrast, the presence of other divalent metal ions either slightly enhance fluorescence (e.g., $Mg^{2+}$, $Mn^{2+}$ and $Cd^{2+}$) of the test sample or exhibit far less quenching of fluorescence than $Hg^{2+}$. (See, e.g., FIG. 4.)

Sensitivity for mercury is enhanced by the use of aqueous test samples and control samples. By way of illustration only, good results may be obtained with aqueous acetonitrile solutions in which the amount of water by volume ranges from about 25% to about 60%. However, smaller or larger amounts of water may also be used so long as at least a two-fold difference in fluorescence is maintained between $Hg^{2+}$ and the metal ion of interest. It is well within the skill in the art based on the present disclosure to select a suitable volume percentage of water to enhance selectivity of mercury ion detection. Concentrated solutions can be diluted using suitable solvents prior to testing.

In the present methods, the fluorescence of a compound of Formula I may be detected by essentially any suitable fluorescence detection device. Such devices typically include a light source for excitation of the fluorophore and a sensor for detecting emitted light. In addition, fluorescence detection devices may contain a means for controlling the wavelength of the excitation light and a means for controlling the wavelength of the light detected by the sensor. Such means are referred to generically as filters and can include diffraction gratings, dichroic mirrors, or filters. Examples of suitable devices include fluorometers, spectrofluorometers and fluorescence microscopes. Many such devices are commercially available from companies such as Perkin-Elmer, Hitachi, Nikon, Molecular Dynamics, or Zeiss. In certain embodiments, the device is coupled to a signal amplifier and a computer for data processing.

Using the above devices, the fluorescence excitation and emission spectra of compounds of Formula I may be determined by standard techniques in the art. Thus, suitable excitation and emission wavelengths may be readily selected by those of skill in the art for the application at hand. Generally, compounds of Formula I may be excited at a wavelength ranging from about 250 nm to about 300 nm and the emission monitored at wavelength from about 285 nm to about 400 nm (so long as the emission wavelength is longer than the excitation wavelength). For example, L may be excited at a wavelength of about 275 nm and monitored at an emission wavelength of about 310 nm.

In some embodiments, metal ion binding by calix[4]arene compounds of the present technology may be detected by alternate techniques including, but not limited to, absorption spectroscopy, ESI mass spectrometry and/or NMR. Examples of absorption spectroscopy techniques that may be used include, but are not limited to, infrared spectroscopy, microwave spectroscopy, and UV-visible spectroscopy.

In some embodiments of the present technology, the complex species formed between compound of Formula I and $Hg^{2+}$ can be isolated and characterized. In some embodiments, the complex species can be characterized using techniques known in the art such as transmission electron microscopy (TEM), atomic force microscopy (AFM), and scanning electron microscopy (SEM) and powder XRD studies. In some embodiments, the binding characteristics of $Hg^{2+}$ towards compounds of Formula I can be established based on the DFT computational calculations. In some embodiments, the complex species has a 1:1 ratio of compound of Formula I and $Hg^{2+}$.

4. METHODS OF PREPARATION

The compounds of this technology can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis,* 3rd Edition, Wiley, New York (1999), and references cited therein.

Furthermore, the compounds of this technology may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this technology, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5, and Supplementals (Elsevier Science Publishers, 1989), Organic Reactions, Volumes 1-40 (John Wiley and Sons, 1991), March's Advanced Organic Chemistry, (John Wiley and Sons, 5$^{th}$ Edition, 2001), and Larock's Comprehensive Organic Transformations (VCH Publishers Inc., 1989).

The compounds of Formula I may be prepared by, for example, the synthetic protocol illustrated in Scheme 1.
In Scheme 1, the substituents $R^1$, $R^2$ and $R^3$ areas defined herein. p-Substituted calix[4]arene V can be purchased from
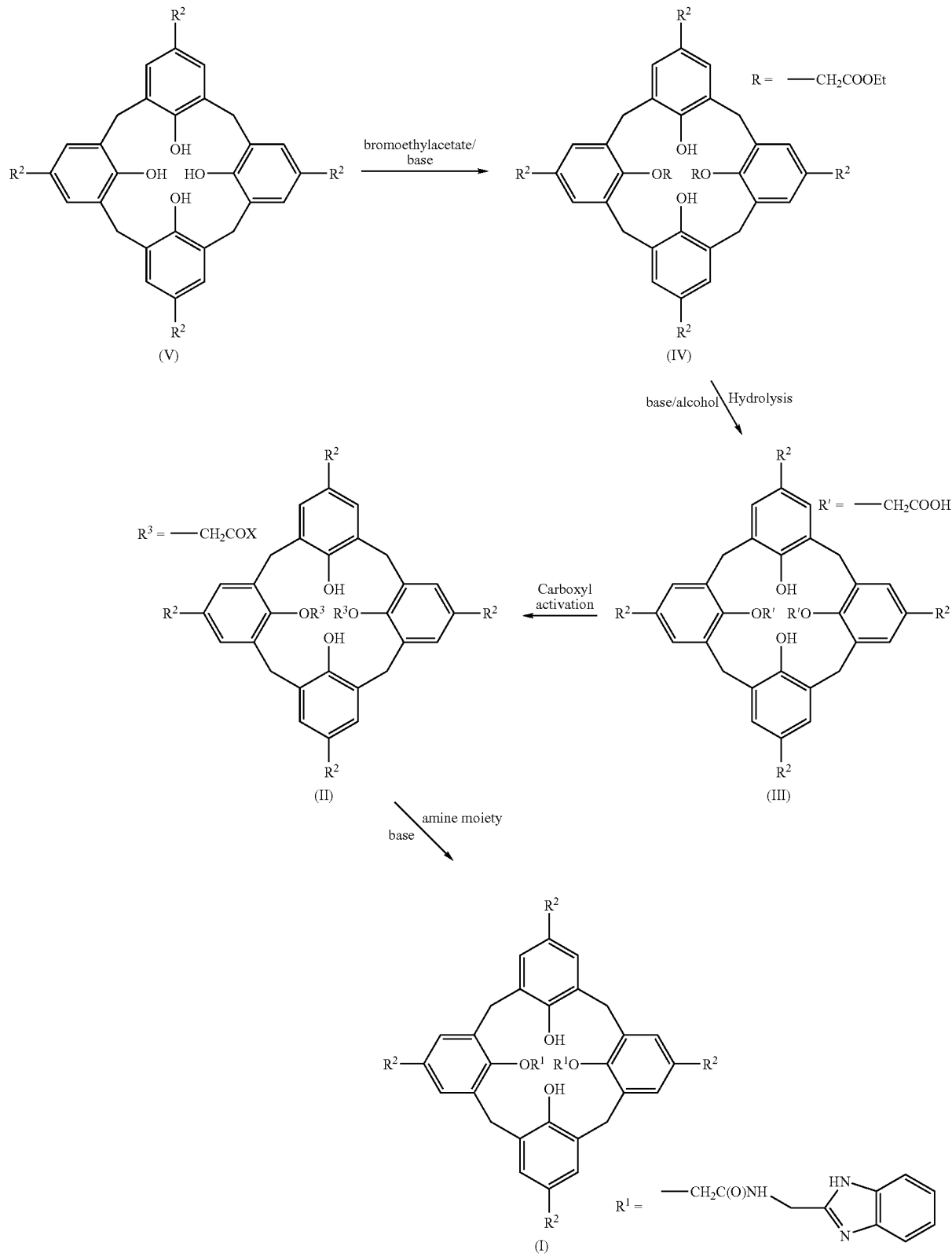
Scheme 1 commercial sources or prepared according to the procedure given by Gutsche and co-workers (*J. Am. Chem. Soc.*, 1981, 103, 3782) or by appropriate modification thereof. The compound of Formula V may be reacted with ethyl 2-bromoacetate or similar electrophilic acetates in the presence of a suitable base to produce the ester IV. Example of such bases include, but are not limited to, potassium carbonate, potassium bicarbonate, sodium hydroxide, potassium hydroxide, and the like. The reaction mixture may be heated, e.g., refluxed, if desired.

Ester hydrolysis of IV in the presence of a suitable base and an alcohol results in acid III. Example of alcohol includes, but is not limited to, ethanol, methanol, i-propanol, and the like. In some embodiments aqueous alcoholic solutions are used. The reaction mixture may be heated or refluxed, if desired.

The acid III may be activated for amide bond formation. For example, acid III can be transformed into an acid halide such as an acid chloride by, e.g., treatment with thionyl chloride in the presence of a suitable solvent to give the acid chloride of Formula II. The reaction may be heated or refluxed, if desired. It is to be understood that other chlorinating agents known in the art can also be used in this reaction, such as, but not limited to, phosphorus trichloride ($PCl_3$), and phosphorus pentachloride ($PCl_5$).

The acid chloride II is then treated with a suitable amine moiety in the presence of a suitable base and a solvent to result in compounds of Formula I. The amine derivatives include dibenzylamine, 2-aminomethylpyridine, methyl ester of phenylalanine and 2-aminomethyl benzimidazole. Examples of base include, but are not limited to, tertiary amines or a pyridine compound, such as, triethylamine, diisopropylethylamine, pyridine, and dimethylaminopyridine. Examples of solvent include, but are not limited to, tetrahydrofuran, diethylether, acetonitrile, carbon tetrachloride, dimethyl sulfoxide, dimethylformamide, or dioxane.

Alternatively, the acid III may be activated for amide bond formation and coupled to a suitable amine using standard peptide coupling reactions. Thus, the acid III may be reacted with a coupling agent such as dicyclohexylcarbodiimide (DCC), 1-ethyl-3-(3-dimethylaminopropyl)carbodiimide (EDCI), optionally in the presence of 1-hydroxybenzotriazole (HOBt) or 1-hydroxy-7-azabenzotriazole (HOAt), and the suitable amine to give the compound of Formula I directly. Acid III may also be converted to a mixed anhydride, or active ester using standard techniques (see, e.g., Bodanszky M. and Bodanzsky, A., *The Practice of Peptide Synthesis*, Springer-Verlag, New York (1984), incorporated herein by reference in its entirety).

Upon reaction completion, each of compounds of Formula I, II, III, IV and V can be recovered by conventional techniques such as neutralization, extraction, precipitation, chromatography, filtration, recrystallization and the like. In some embodiments, the compounds are purified using high-performance liquid chromatography. In some embodiments, the compounds are used as is in the next reaction.

It is to be understood that the synthetic method in Scheme I is for illustration purposes only and other deviations or modifications from the scheme that result in the compounds of Formula I are well within the skill of a person of ordinary skill in the art.

Thus, in one aspect of the present technology, there is provided a method for preparing a compound of the present technology by contacting 2-aminomethyl benzimidazole in a presence of a suitable base and a solvent with a compound of Formula II:

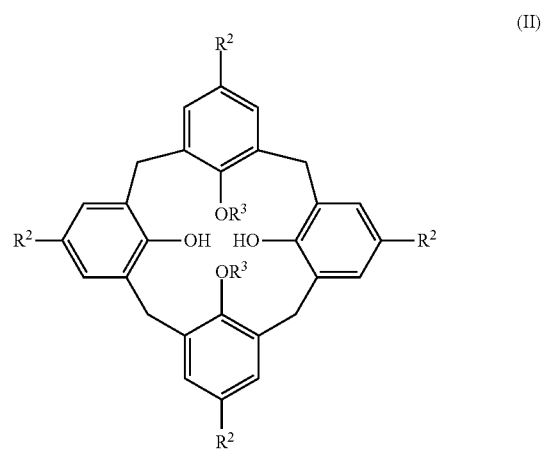

(II)

wherein $R^3$ is —$CH_2COX$ and X is a halide. Alternatively, if $R^3$ is —$CH_2COOH$, a coupling agent may be used to couple the compound of Formula III directly to the amine.

In some embodiments, the suitable base is a tertiary amine or a pyridine compound. In some embodiments, the suitable base is selected from the group consisting of triethylamine, diisopropylethylamine, pyridine, and dimethylaminopyridine.

In some embodiments, the solvent is tetrahydrofuran, diethyl ether, acetonitrile, carbon tetrachloride, dimethyl sulfoxide, dimethylformamide, or dioxane.

In another aspect, there are provided methods for preparing a compound of Formula I including contacting 2-aminomethyl benzimidazole in the presence of a suitable base with a compound of Formula II:

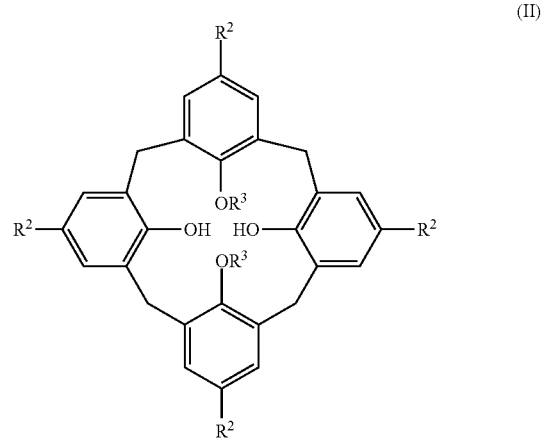

(II)

wherein $R^3$ is —$CH_2COX$ and X is a halide.

In some embodiments, the suitable base is a tertiary amine or a pyridine compound. In some embodiments, the suitable base is selected from the group consisting of triethylamine, diisopropylethylamine, pyridine, and dimethylaminopyridine.

In another aspect, there are provided methods for preparing a compound of Formula I including activating carboxyl groups of Formula II for amide bond formation and reacting the activated compound of Formula II with 2-aminomethyl benzimidazole to give the compound of Formula I, wherein the compound of Formula II is:

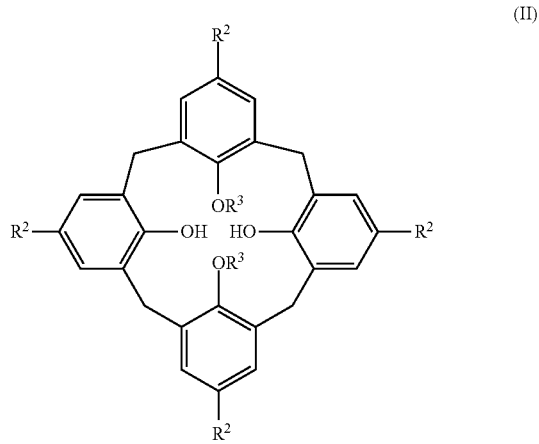

wherein $R^3$ is —$CH_2COOH$.

In some embodiments, the compound of Formula II is activated by forming an halide from each $R^3$ group. In some embodiments, the compound of Formula II is activated by forming an active ester, a mixed anhydride or by use of a peptide coupling reagent. In some embodiments, the coupling reagent is DCC or EDCI. In some embodiments, the coupling reaction is conducted in the presence of HOBt or HOAt Salts of the disclosed compounds are considered within the scope of the present technology. When such compound has a basic group, such as, for example, an amino group, pharmaceutically acceptable salts can be formed with inorganic acids (such as perchloric acid, hydrochloric acid, sulfuric acid, and phosphoric acid), organic acids (e.g., formic acid, acetic acid, citric acid, succinic acid, trifluoroacetic acid, methanesulfonic acid, and p-toluenesulfonic acid) or acidic amino acids (such as aspartic acid and glutamic acid).

EXAMPLES

The present technology is further illustrated by the following examples, which should not be construed as limiting in any way. The following definitions are used herein.

Å Angstrom
$CH_3CN$ Acetonitrile
$CHCl_3$ Chloroform
$CH_3OH$ Methanol
d Doublet
DCC 1,3-Dicyclohexylcarbodiimide
EDCI 1-Ethyl-3-(3'-dimethylaminopropyl) carbodiimide hydrochloride
ESI Electron spray ionization
FTIR Fourier transform infra-red
g Gram
HOAt 1-Hydroxy-7-azabenzotriazole
HOBt 1-Hydroxybenzotriazole
MHz Megahertz
L Microliter
mL Milliliter
M Micromolar
MP Melting point
MS Mass spectroscopy
m/z Mass/charge
nm Nanometer
NMR Nuclear magnetic resonance
ns Nanosecond(s)
ppb Parts per billion
ppm Parts per million
s Singlet
t Triplet
TLC Thin layer chromatography
v/v Volume/volume Materials and Methods All the metal salts used for the titrations provided herein were perchlorates with Formula, $M(ClO_4)_2 \cdot xH_2O$. All the perchlorate salts were procured from Sigma Aldrich Chemical Co., U.S.A. All the solvents used were of analytical grade and were purified and dried by routine procedures immediately before use. Distilled and deionized water was used in the studies.

$^1H$ and $^{13}C$ NMR spectra were measured on a Varian Mercury NMR spectrometer working at 400 MHz. The mass spectra were recorded on Q-TOF micromass (YA-105) using electrospray ionization method. The time-resolved single photon counting (TCSPC) was measured on fluorocube time-resolved fluorescence spectrometer from IBH, UK.

Steady state fluorescence spectra were measured on Perkin-Elmer LS55. The absorption spectra were measured on Shimadzu UV2101 PC. The elemental analyses were performed on ThermoQuest microanalysis. FT IR spectra were measured on Perkin-Elmer spectrometer using KBr pellets. Single crystal X-ray diffraction data were measured on OXFORD XCALIBUR-S CCD machine. TEM experiments were performed on a JEOL 1200 EX transmission electron microscope operating at 80-120 kV. AFM studies were performed in multimode Veeco Dimensions 3100 SPM with Nanoscope IV controller instrument. SEM was performed on a Hitachi S3400 cold-cathode Field Emission Scanning Electron Microscope (Hitachi High Technologies America, Inc., Pleasanton, Calif.). All the computational calculations were performed using Gaussian 03 package.

Synthetic and analytical methods may be carried out as described in R. Joseph, B. Ramanujam, A. Acharya, A. Khutia and C. P. Rao, *J. Org. Chem.*, 2008, 73, 5745-58, the entire contents of which are herein incorporated by reference for any and all purposes.

Example 1
Scheme 2 Synthesis of 2-aminomethyl benzimidazole derivative of calix[4]arene 5,11,17,23-tetra-tert-butyl-25,27-bis((2-aminomethyl benzimidazole)carbonylmethoxy)-26,28-dihydroxycalix[4]arene, (L)
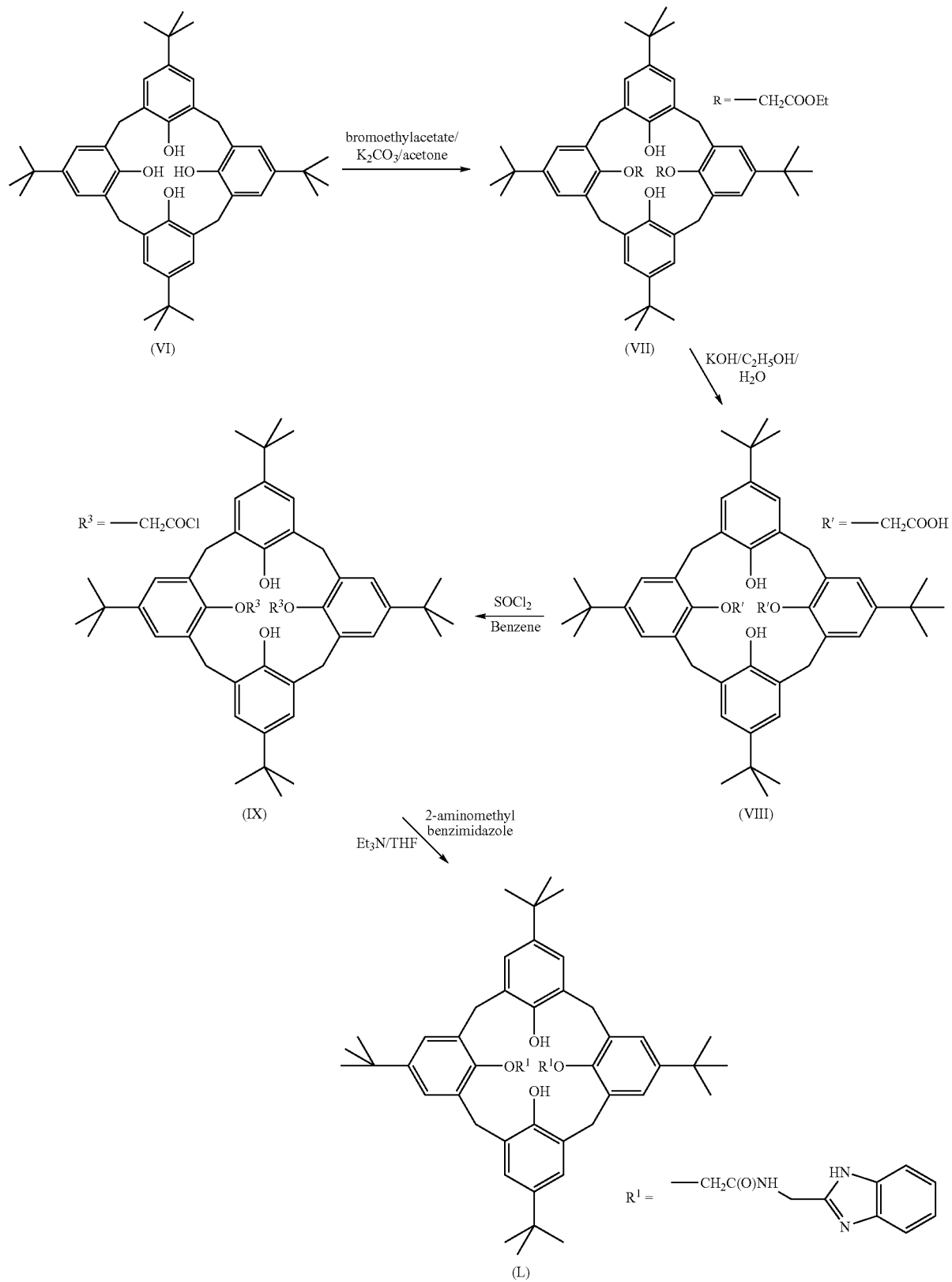

Synthesis of VI:

p-Tert-butyl-calix[4]arene, VI, is synthesized by the condensation of p-tert-butyl-phenol with formaldehyde in presence of NaOH per the procedure given by Gutsche and co-workers (*J. Am. Chem. Soc.*, 1981, 103, 3782).

Synthesis and Characterization of VII:

A mixture of V (10 g, 15.4 mmol), potassium carbonate (4.26 g, 30.8 mmol), and ethyl bromoacetate (5.14 mL, 30.8 mmol) were added to dry acetone (1.6 L) and the mixture was stirred and heated at reflux for 15 h under nitrogen atmosphere. The cooled reaction mixture was filtered through a bed of celite and the filtrate and dichloromethane washings of the celite were combined and concentrated to dryness. Recrystallization of the residue from ethanol yielded the diester. Yield (9.86 g, 78%).

$^1$H NMR (CDCl$_3$, δ ppm): 0.98 (s, 18H, C(CH$_3$)$_3$), 1.26 (s, 18H each, C(CH$_3$)$_3$), 1.34 (t, 6H, CH$_2$—CH$_3$, J=7.02 Hz), 3.32 (d, 4H, Ar—CH$_2$—Ar, J=13.4 Hz), 4.30 (q, 4H, CH$_2$—CH$_3$), 4.45 (d, 4H, Ar—CH$_2$—Ar, J=13.2 Hz), 4.73 (s, 4H, OCH$_2$CO), 6.82 (s, 4H, Ar—H), 7.02 (s, 4H, Ar—H), 7.06 (s, 2H, OH).

Synthesis and Characterization of VIII:

A mixture of the diester, VII, (10 g, 12.2 mmol) and 15% aq. sodium hydroxide (32 mL) in ethanol (500 ml) were stirred and heated under reflux for 24 h and the reaction mixture was evaporated under reduced pressure to yield white residue. The residue was diluted (suspension) with cold water (500 ml) and hydrochloric acid (3 N) was added with vigorous mixing until pH 1 was reached. The solid was filtered, dried in air and was further dissolved in chloroform. The solution was washed with hydrochloric acid (3 N) and brine, dried and concentrated to afford the diacid product, VIII. VIII was recrystallized from aq. acetone (acetone:water, 7:3 v/v). Yield (7.92 g, 85%).

1H NMR (CDCl$_3$, δ ppm): 1.10 (s, 18H each, C(CH$_3$)$_3$), 1.30 (s, 18H each, C(CH$_3$)$_3$), 3.46 (d, 4H, Ar—CH$_2$—Ar, J=13.74 Hz), 4.13 (d, 4H, Ar—CH$_2$—Ar, J=13.44 Hz), 4.70 (s, 4H, OCH$_2$CO), 6.99 (s, 4H, Ar—H), 7.07 (s, 4H, Ar—H).

Synthesis and Characterization of L:

To dry benzene (100 mL), p-tert-butylcalix[4]arene diacid, VIII, (4.0 g) and SOCl$_2$ (6 mL) were added and refluxed under nitrogen atmosphere for 4 h. The solvent and residual SOCl$_2$ were removed under reduced pressure, and this yielded diacid chloride IX, as off white solid and was used in situ for the preparation of the receptor molecules L.

A suspension of 2-(aminomethyl)benzimidazole 2HCl (2.73 g, 12.4 mmol) and Et$_3$N (6 mL, 43.1 mmol) was stirred in dry THF (100 mL) under argon atmosphere. Diacid chloride, IX (4.32 g, 5.34 mmol) in dry THF (50 mL) was added dropwise to this reaction mixture. Immediately, a yellowish precipitate was formed and stirring was continued for 48 hrs at room temperature. After filtration, the filtrate was concentrated to dryness. A yellow solid was obtained which was extracted with CHCl$_3$, washed with water and then with brine, and the organic layer was dried with anhydrous MgSO$_4$. Filtrate was concentrated to dryness and recrystallized from EtOH/CHCl$_3$ to get L as a white solid. Yield (55%, 2.95 g).

C$_{64}$H$_{74}$N$_6$O$_6$ (1023.29): Anal. (% found) C, 67.58; H, 7.50; N, 6.76, C$_{64}$H$_{74}$N$_6$O$_6$.2C$_2$H$_5$OH. CHCl$_3$ (% requires) C, 67.11; H, 7.11; N, 6.80).

FTIR: (KBr, cm$^{-1}$): 1679 (C=O), 3380 (OH);

$^1$H NMR: (CDCl$_3$, δ ppm): 0.98 (s, 18H, (C(CH$_3$)$_3$), 1.25 (s, 18H, (C(CH$_3$)$_3$), 3.28 (d, 4H, Ar—CH$_2$—Ar, J=13.30 Hz), 3.96 (d, 4H, Ar—CH$_2$—Ar, J=13.30 Hz), 4.40 (s, 4H, —CH$_2$CONH—), 4.88 (d, 4H, —CONHCH$_2$—, J=5.50 Hz), 6.8 (s, 4H, Ar—H), 7.03 (s, 4H, Ar—H), 7.23-7.25 (m, 4H, benzimidazole), 7.53-7.55 (m, 4H, benzimidazole), 7.45 (s, 2H, —OH), 8.95 (t, 2H, —NH, J=5.19). $^{13}$C NMR: (CDCl$_3$, 400 MHz δ ppm): 31.10, 31.8 (C(CH$_3$)$_3$), 32.1 (Ar—CH$_2$—Ar), 34.0, 34.2 (C(CH$_3$)$_3$), 37.3 (CH$_2$-benzimidazole), 73.8 (OCH$_2$CO), 114.9, 124.1, 125.5, 126.1, 127.4, 135.5, 135.9, 142.7, 148.1, 149.2, 149.8, 152.0, (benzimidazole and calix-Ar—C), 170.6 (C=O). m/z (ES-MS) 1023.72 ([M]$^+$100%), 1024.7 ([M+H]$^+$35%).

Example 2

Crystallization of 2-Aminomethyl Benzimidazole Derivative of Calix[4]arene (L)

Single crystals of L were obtained by slow evaporation of the solvent mixture (EtOH/CHCl$_3$) at room temperature. An X-ray crystal structure of L was obtained as illustrated the ORTEP diagram, shown in FIG. 1. The crystal structure clearly shows the presence of a cone conformation of calix [4]arene and is in conformity with the result obtained based on NMR analysis. The crystal structure also confirmed the formation of 1,3-arms through the amide linkages disposed on the same side of the calix[4]arene at the lower rim to result in binding cores. In all these lower-rim diderivatives, there are two intra-rim O—H..O hydrogen bonds present to maintain the cone conformational structure.

Below are the metric parameters obtained from the single crystal X-ray structure of L.

Crystallographic Data:

|  | L |
|---|---|
| Empirical Formula | C$_{64}$H$_{74}$N$_6$O$_6$•3(C$_2$H$_5$OH) |
| Temperature (K) | 150 |
| Crystal System | Triclinic |
| Space group | P (No. 2) |
| a/Å | 13.1060(14) |
| b/Å | 13.467(4) |
| c/Å | 21.4629(19) |
| α/° | 76.369(16) |
| β/° | 74.335(9) |
| γ/° | 73.248(16) |
| Volume/Å$^3$ | 3441.1(12) |
| Z | 2 |
| Reflections collected | 34518 |
| Independent reflections | 11985 |
| R$_{int}$ | 0.042 |
| Reflections used$^b$ | 6118 |
| Parameters | 797 |
| Final R | 0.0710 |
| R$^{rc}$ | 0.2260 |

$b=[I>2.0σ(I)]$ $c=1/[s^2(F_o^2)+(0.1133P)^2+1.8869P]$ where $P=(F_o^2+2F_c^2)/3$.

TABLE 1

| Selected bond distances | |
|---|---|
| a...b | Distance (Å) |
| O1...C9 | 1.239 (4) |
| O2...C10 | 1.437 (4) |
| O2...C11 | 1.403 (4) |
| O3...C31 | 1.378 (4) |
| O4...C42 | 1.406 (4) |
| O4...C55 | 1.437 (4) |
| O5...C56 | 1.231 (4) |
| O6...C53 | 1.386 (4) |

TABLE 1-continued

Selected bond distances

| a...b | Distance (Å) |
|---|---|
| N1...C7 | 1.357 (5) |
| N1...C1 | 1.392 (6) |
| N2...C6 | 1.398 (5) |
| N2...C7 | 1.320 (5) |
| N3...C9 | 1.343 (4) |
| N3...C8 | 1.466 (5) |
| N4...C60 | 1.391 (5) |
| N4...C58 | 1.358 (6) |
| N5...C58 | 1.328 (5) |
| N5...C59 | 1.395 (6) |
| N6...C57 | 1.460 (4) |
| N6...C56 | 1.342 (4) |
| C24...C25 | 1.543 (6) |
| C24...C29 | 1.397 (6 |
| C25...C28 | 1.509 (8) |
| C25...C26 | 1.511 (9) |
| C25...C27 | 1.530 (8) |
| C29...C30 | 1.396 (5) |
| C30...C31 | 1.398 (5) |
| C30...C32 | 1.515 (6) |
| C32...C33 | 1.517 (5) |
| C33...C34 | 1.394 (5) |
| C33...C42 | 1.396 (5) |
| C34...C35 | 1.396 (5) |
| C35...C40 | 1.403 (5) |
| C35...C36 | 1.534 (5) |
| C36...C37 | 1.540 (8) |
| C36...C39 | 1.521 (8) |
| C36...C38 | 1.540 (7) |
| C40...C41 | 1.394 (5) |
| C41...C42 | 1.400 (5) |
| C41...C43 | 1.527 (5) |
| C43...C44 | 1.514 (5) |
| C44...C53 | 1.400 (4) |
| C44...C45 | 1.392 (5) |
| C45...C46 | 1.398 (6) |
| C46...C47 | 1.533 (6) |
| C46...C51 | 1.392 (6) |
| C47...C49 | 1.459 (10) |
| C1...C2 | 1.408 (6) |
| C1...C6 | 1.394 (6) |
| C2...C3 | 1.393 (8) |
| C3...C4 | 1.393 (7) |
| C4...C5 | 1.365 (7) |
| C5...C6 | 1.403 (6) |
| C12...C54 | 1.513 (5) |
| C13...C14 | 1.391 (5) |
| C14...C19 | 1.393 (5) |
| C14...C15 | 1.538 (5) |
| C15...C18 | 1.532 (8) |
| C15...C16 | 1.490 (7) |
| C15...C17 | 1543 (7) |
| C19...C20 | 1.404 (5) |
| C20...C21 | 1.526 (5) |
| C21...C22 | 1.514 (5) |
| C22...C31 | 1.409 (4) |
| C22...C23 | 1.401 (5) |
| C47...C50 | 1.481 (11) |
| C51...C52 | 1.398 (5) |
| C52...C53 | 1.397 (5) |
| C52...C54 | 1.528 (6) |
| C55...C56 | 1.513 (5) |
| C57...C58 | 1.492 (5) |
| C59...C60 | 1.403 (7) |
| C59...C64 | 1.392 (6) |
| C60...C61 | 1.390 (8 |
| C61...C62 | 1.382 (7) |
| C62...C63 | 1.414 (10) |
| C63...C64 | 1.385 (9) |
| C1...C2 | 1.408 (6) |

TABLE 2

Selected Bond Angles

| a-b-c | Angle (°) |
|---|---|
| C10—O2—C11 | 115.2 (2) |
| C42—O4—C55 | 114.6 (2) |
| C1—N1—C7 | 106.5 (4) |
| C6—N2—C7 | 105.0 (4) |
| C8—N3—C9 | 122.0 (3) |
| C58—N4—C60 | 106.8 (3) |
| C58—N5—C59 | 105.1 (4) |
| C56—N6—C57 | 121.2 (3) |
| N1—C1—C6 | 105.8 (3) |
| C2—C1—C6 | 121.6 (4) |
| N1—C1—C2 | 132.6 (4) |
| C1—C2—C3 | 115.8 (4) |
| C2—C3—C4 | 122.7 (4) |
| C3—C4—C5 | 121.0 (5) |
| C4—C5—C6 | 118.2 (4) |
| C11—C20—C19 | 117.0 (3) |
| C11—C20—C21 | 123.5 (3) |
| C19—C20—C21 | 119.4 (3) |
| C20—C21—C22 | 110.5 (3) |
| C23—C22—C31 | 117.7 (3) |
| C21—C22-01 | 120.8 (3) |
| C21—C22—C23 | 121.4 (3) |
| C22—C23—C24 | 123.5 (4) |
| C25—C24—C29 | 121.1 (4) |
| C23—C24—C29 | 116.5 (3) |
| C23—C24—C25 | 122.2 (4) |
| C24—C25—C28 | 112.4 (4) |
| C27—C25—C28 | 107.1 (5) |
| C24—C25—C27 | 107.6 (4) |
| C26—C25—C28 | 106.7 (5) |
| C26—C25—C27 | 111.1 (5) |
| C24—C25—C26 | 112.0 (4) |
| C24—C29—C30 | 122.9 (4) |
| C31—C30—C32 | 120.5 (3) |
| C29—C30—C32 | 120.6 (4) |
| C29—C30—C31 | 118.6 (4) |
| C22—C31—C30 | 120.8 (3) |
| O3—C31—C30 | 123.1 (3) |
| O3—C31—C22 | 116.1 (3) |
| C30—C32—C33 | 111.0 (3) |
| C34—C33—C42 | 118.0 (3) |
| C32—C33—C42 | 122.7 (3) |
| C32—C33—C34 | 119.3 (3) |
| C48—C47—C50 | 105.6 (6) |
| C46—C47—C49 | 113.9 (5) |
| C49—C47—C50 | 114.1 (7) |
| C46—C51—C52 | 123.4 (4) |
| C53—C52—C54 | 121.1 (3) |
| C51—C52—C53 | 117.9 (4) |
| C51C52—C54 | 120.8 (4) |
| O6—C53—C44 | 116.5 (3) |
| O6—C53—C52 | 122.4 (3) |
| C44—C53—C52 | 121.1 (3) |
| C12—C54—C52 | 110.6 (3) |
| O4—C55—C56 | 110.8 (3) |
| O5—C56—C55 | 119.5 (3) |
| O5—C56—N6 | 124.4 (3) |
| N6—C56—C55 | 116.1 (3) |
| N6—C57—C58 | 113.9 (3) |
| N4—C58—C57 | 123.2 (3) |
| N5—C58—C57 | 123.6 (4) |
| N4—C58—N5 | 113.1 (3) |
| N5—C59—C60 | 109.4 (4) |
| N5—C59—C64 | 130.6 (4) |
| C1—C6—C5 | 120.7 (4) |
| N2—C6—C5 | 129.9 (4) |
| N2—C6—C1 | 109.4 (4) |
| N2—C7—C8 | 123.7 (4) |
| N1—C7—N2 | 113.4 (4) |
| N1—C7—C8 | 122.8 (4) |
| N3—C8—C7 | 109.8 (3) |
| N3—C9—C10 | 115.9 (3) |
| O1—C9—N3 | 123.4 (3) |
| O1—C9—C10 | 120.7 (3) |
| O2—C10—C9 | 110.2 (3) |
| O2—C11—C12 | 118.3 (3) |

TABLE 2-continued

Selected Bond Angles

| a-b-c | Angle (°) |
|---|---|
| C12—C11—C20 | 122.2 (3) |
| O2—C11—C20 | 119.3 (3) |
| C11—C12—C13 | 118.1 (3) |
| C11—C12—C54 | 122.4 (3) |
| C13—C12—C54 | 119.3 (3) |
| C12—C13—C14 | 122.4 (3) |
| C13—C14—C15 | 122.2 (3) |
| C13—C14—C19 | 117.6 (3) |
| C15-O4-O9 | 120.2 (3) |
| C14—C15—C17 | 109.4 (3) |
| C16—C15—C18 | 110.1 (5) |
| C14—C15—C16 | 113.1 (3) |
| C14—C15—C18 | 109.1 (3) |
| C16—C15—C17 | 106.6 (5) |
| C17—C15—C18 | 108.5 (4) |
| C14—C19—C20 | 122.8 (3) |
| C33—C34—C35 | 122.5 (3) |
| C34—C35—C40 | 116.8 (3) |
| C36—C35—C40 | 120.2 (4) |
| C34—C35—C36 | 123.0 (3) |
| C35—C36—C38 | 108.4 (3) |
| C37—C36—C39 | 109.5 (4) |
| C35—C36—C39 | 111.9 (4) |
| C35—C36—C37 | 109.0 (4) |
| C38—C36—C39 | 108.2 (4) |
| C37—C36—C38 | 109.8 (5) |
| C35—C40—C41 | 123.5 (4) |
| C40—C41—C42 | 116.8 (3) |
| C40—C41—C43 | 119.5 (3) |
| C42—C41—C43 | 123.7 (4) |
| O4-C42—C41 | 119.5 (3) |
| C33—C42—C41 | 122.5 (3) |
| O4-C42—C33 | 117.8 (3) |
| C41—C43—C44 | 110.3 (3) |
| C43—C44—C53 | 120.7 (3) |
| C45—C44—C53 | 118.2 (3) |
| C43—C44—C45 | 121.0 (3) |
| C44—C45—C46 | 123.3 (4) |
| C47—C46—C51 | 122.6 (4) |
| C45—C46—C51 | 116.1 (4) |
| C45—C46—C47 | 121.3 (4) |
| C48—C47—C49 | 100.0 (6) |
| C46—C47—C48 | 107.5 (5) |
| C46—C47—C50 | 114.2 (5) |
| C59—C64—C63 | 117.4 (5) |
| C60—C59—C64 | 120.0 (4) |
| C59—C60—C61 | 122.9 (4) |
| N4—C60—C61 | 131.4 (4) |
| N4—C60—C59 | 105.6 (4) |
| C60—C61—C62 | 116.9 (5) |
| C61—C62—C63 | 120.6 (7) |
| C62—C63—C64 | 122.2 (5) |

TABLE 3

Selected Hydrogen Bonds

| Bond | D-H (Å) | H-A (Å) | D-A (Å) | D-H-A (°) |
|---|---|---|---|---|
| O3—H3...O4 | 0.8200 | 2.0800 | 2.826(3) | 151.00 |
| N3—H3N...O3 | 0.85(4) | 2.20(4) | 3.036(4) | 169(4). |
| N4—H4N...N2 | 1.00(4) | 1.87(4) | 2.863(5) | 180(5) |
| O6—H6...O2 | 0.8200 | 2.0900 | 2.826(3) | 149.00 |
| N6—H6N...O6 | 0.97(4) | 2.11(4) | 3.050(4) | 163(3) |
| C57—H57A...O1 | 0.9700 | 2.4300 | 3.376(5) | 166.00 |
| C57—H57B...O5 | 0.9700 | 2.4500 | 3.287(5) | 145.00 |

Example 3

Synthesis, and Isolation of the $Hg^{2+}$ Complex of Calix[4]arene Derivative L $Hg(ClO_4)_2$ (0.094 g, 0.235 mmols) was dissolved in $CH_3OH$ (5 mL) and was added to the compound L (0.20 g, 0.196 mmols) in $CHCl_3$. The solution was stirred overnight followed by refluxing for 12 h. The resulting solution was concentrated, washed with minimum amount of methanol and dried under vacuum. Yield (80%, 0.22 g).

$^1H$ NMR: ($CDCl_3$, 400 MHz δ ppm): 1.10 (s, 18H, $C(CH_3)_3$), 1.14 (s, 18H, $C(CH_3)_3$), 3.43 (d, 4H, Ar—$CH_2$—Ar, J=12.50 Hz), 4.10 (d, 4H, Ar—$CH_2$—Ar, J=12.50 Hz), 4.65 (s, 4H, —$CH_2CONH$—), 5.33 (s, 4H, —$CONHCH_2$—), 7.10 (s, 4H, Ar—H), 7.13 (s, 4H, Ar—H), 7.52 (m, 4H, benzimidazole), 7.76 (s, 2H, benzimidazole), 8.19 (s, 2H, —OH), 8.27 (m, 2H, benzimidazole), 9.75 (s, 2H, CONH), 14.56 (s, 2H, —NH-benzimidazole). Anal. (% found) C, 53.02; H, 6.41; N, 5.57, Hg 12.92. $C_{64}H_{74}N_6O_6 \cdot 4C_2H_5OH \cdot Hg(ClO_4)_2$ (% required) C, 53.41; H, 6.10; N, 5.21, Hg 12.49. ES MS 1231.77 ($[M+Hg+Li]^+$) UV-vis spectral data λ, nm (∈, mole·lit$^{-1}$·cm$^{-1}$): 263 (13932); 270 (18314); 277 (17753); 292 (5168).

Example 4

Characterization of the $Hg^{2+}$ Complex of Calix[4]arene Derivative (L) Using Transmission Electron Microscopy (TEM), Scanning Electron Microscopy (SEM) and Atomic Force Microscopy (AFM)

In order to confirm the structural changes that exist at nano level between the receptor L and its $Hg^{2+}$ complex, studies were carried out by scanning electron microscopy (SEM) and atomic force microscopy (AFM). Whereas transmission electron microscopy (TEM), atomic force microscopy (AFM), and scanning electron microscopy (SEM) provided the nanostructural behavior of L, the TEM and SEM demonstrated that the mercury complex has different characteristics when compared to L. The TEM, SEM, and powder XRD studies revealed that whereas L is crystalline, that of the mercury complex is not, perhaps a reason for not being able to obtain single crystals of the complex. Thus L and its $Hg^{2+}$ complex were distinguishable based on their TEM, SEM and AFM features (FIG. 2 a-c).

The metal ion binding properties of calix[4]arene derivative L were studied in methanol by fluorescence, absorption, ESI MS and NMR.

Example 5

Study of $Hg^{2+}$ Ion Binding with Aminomethyl Benzimidazole Derivative of Calix[4]arene (L) Using Fluorescence Spectroscopy Fluorescence emission spectra were measured by exciting the solutions at 275 nm and the emission spectra were recorded in the 285-400 nm range. Different solvent or solvent combinations were used for fluorescence studies such as, $CH_3OH$, $CH_3CN$, $H_2O:CH_3CN$ (1:1), $H_2O:CH_3CN$ (1:3), and $H_2O:CH_3CN$ (3:2). The fluorescence studies performed in $CH_3OH$ solution were performed using a 50 μL of chloroform solution of L (i.e., the 3 mL solution contains 2.950 mL of $CH_3OH$ and 0.050 mL of $CHCl_3$). All the measurements were made in 1 cm quartz cell and maintained a final L concentration of 10 μM. During the titration, the concentration of metal perchlorate was varied as required to result in requisite mole ratios of metal ion to L and the total volume of the solution was maintained constant at 3 mL in each case by adding appropriate solvent or solvent mixtures. Normalized emission (relative fluorescence) intensities ($I/I_0$) (where, $I_0$ is the intensity with no metal ion addition; I is the intensity at different metal ion to L mole ratios) were plotted against the mole ratio of metal ion to the L. The association constant of the mercury complex formed in the solution were estimated using the standard Benesi-Hildebrand equation.

Figures 3A, 3B:
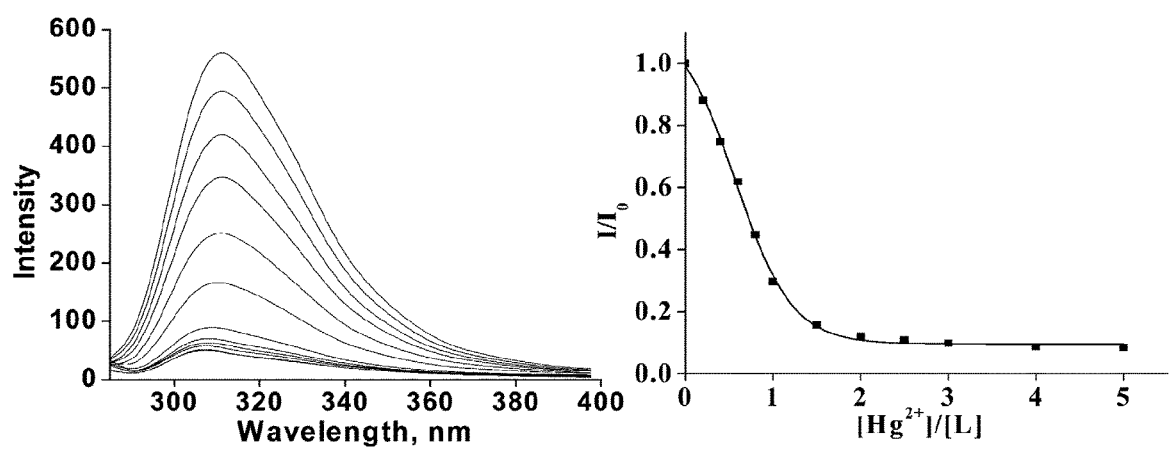
FIG. 3 depicts an illustrative embodiment of a fluorescence titration of 2-aminomethyl benzimidazole derivative of calix[4]arene (compound L) by $Hg^{2+}$: (a) spectral traces during the titration by $Hg^{2+}$ in 1:1 aqueous acetonitrile (b) plot of relative intensity $(I/I_o)$ versus $[Hg^{2+}]/[L]$ mol ratio.
Figure 4:
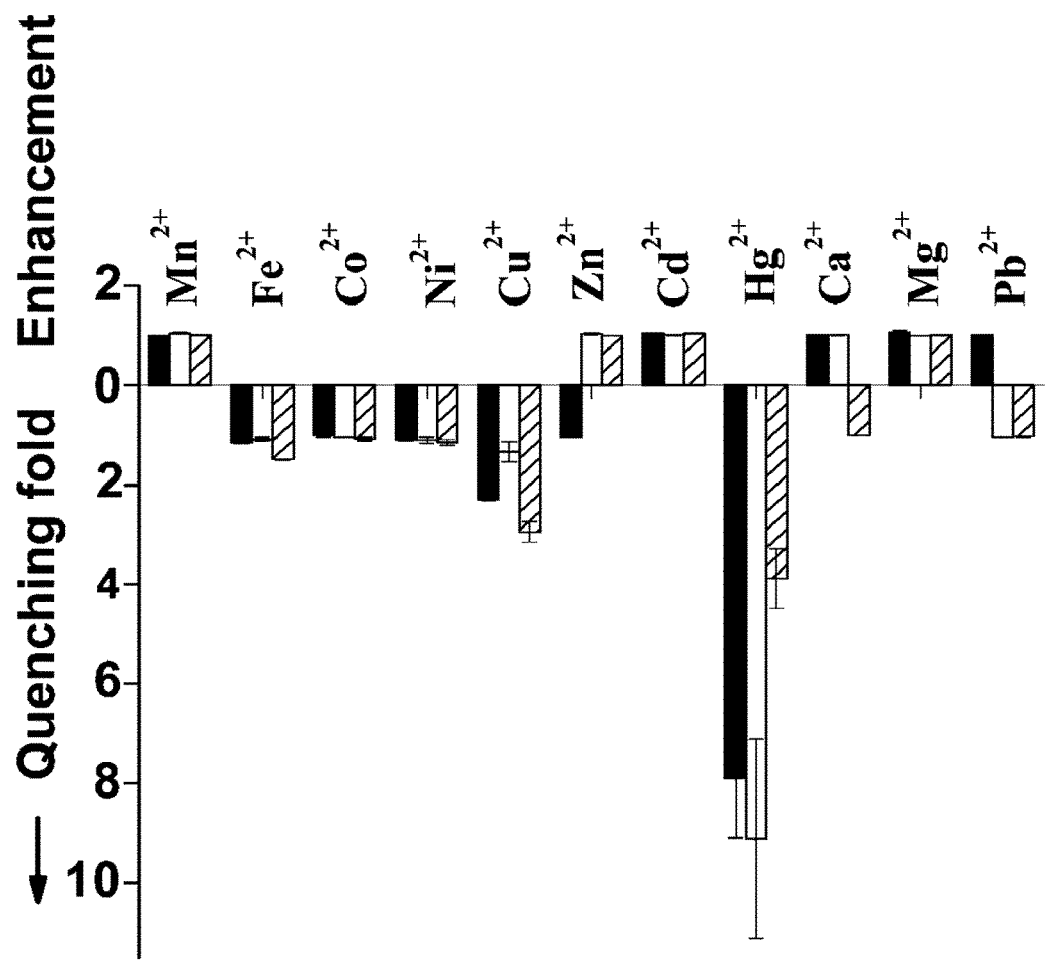
FIG. 4 depicts an illustrative embodiment of a histogram showing the number of times of quenching or enhancement in the relative fluorescence intensity in case of titration of L with different $M^{2+}$ in aqueous acetonitrile solutions. Open columns are for the data in $H_2O:CH_3CN$ of 1:1. Filled columns are for the data in $H_2O:CH_3CN$ of 1:3. Partially filled columns are for the data in $H_2O:CH_3CN$ of 3:2. The error bars were placed based on four different measurements.

In acetonitrile, when L is excited at 275 nm it exhibits a strong emission maximum around 311 nm. To change the polarity of the acetonitrile, different volume ratios of water was added to result in water to acetonitrile ratios of 1:3, 1:1 and 3:2, and the fluorescence titrations between L and $M^{2+}$ were carried out in these aqueous solutions. Typical fluorescence spectra obtained during the titration of L with $Hg^{2+}$ in 50% aqueous solution and the corresponding fluorescence intensity ratio plot are given in FIGS. 3a and 3b. The extent of fluorescence quenching is defined in terms of the quenching fold and the corresponding results obtained from such titrations performed between the L and $M^{2+}$ in aqueous acetonitrile mixtures are shown in FIG. 4.

Figure 5:
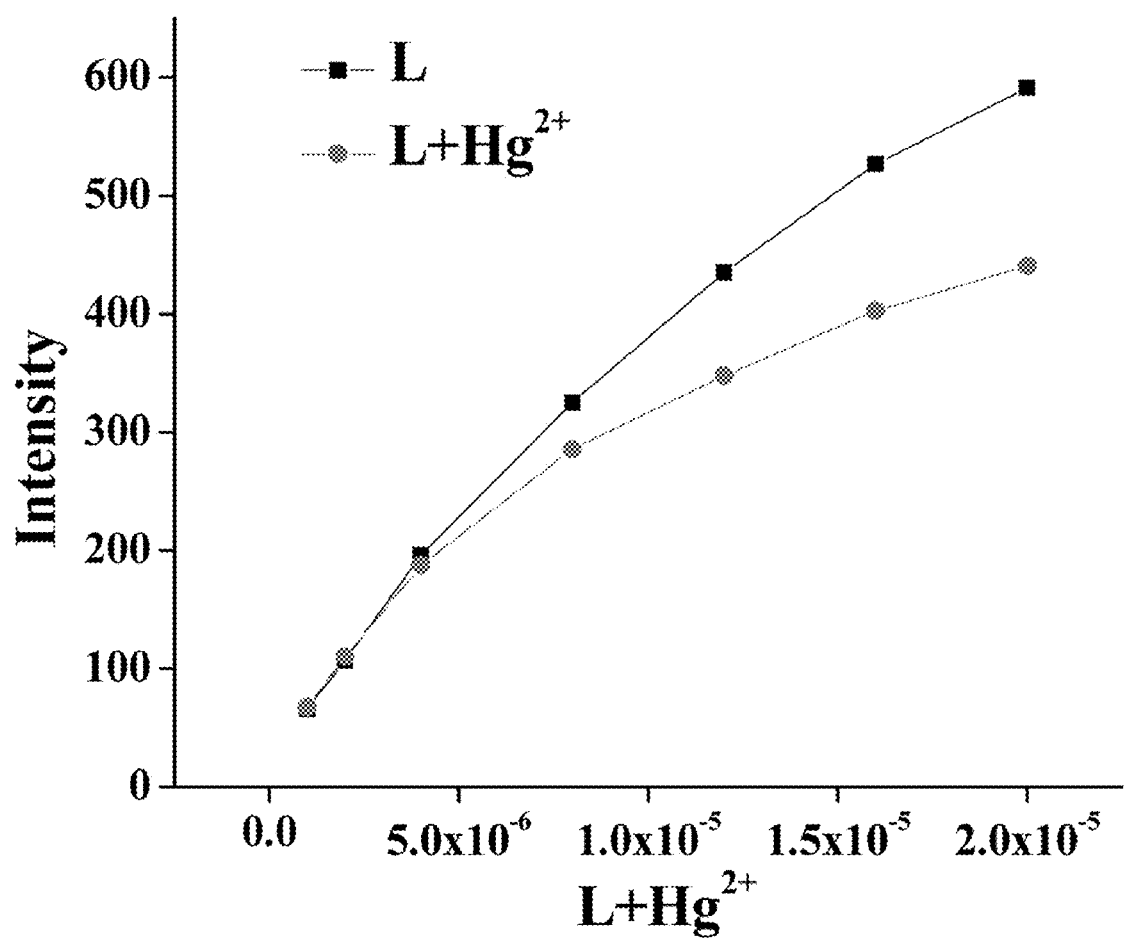
FIG. 5 depicts an illustrative embodiment of fluorescence titrations performed in 1:1 $H_2O:CH_3CN$ mixture by varying $[Hg^{2+}]$ concentration but keeping the $[Hg^{2+}]/[L]$ mole ratio at 1:1.

The species formed between L and $Hg^{2+}$ has been found to be 1:1 based on the present absorption and ESI MS. Even the Job's plot constructed with the fluorescence data supported the formation of 1:1 complex between $Hg^{2+}$ and L. In 50% aqueous solution, a 10-fold quenching was observed only in case of $Hg^{2+}$, whereas all other $M^{2+}$ exhibited almost no quenching in fluorescence intensity. Based on the Benesi-Hildebrand equation, the $K_{ass}$ was found to be 20,966±873 $M^{-1}$. Significant fluorescence intensity changes were observed only in case of the titration of L with $Hg^{2+}$ and not with the other $M^{2+}$ in 1:1 aqueous acetonitrile solution. Fluorescence studies performed in 1:1 aqueous solution by varying $[Hg^{2+}]$ but keeping the $[Hg^{2+}]/[L]$ mole ratio at 1:1 indicated a lower limit detection of 1.4±0.1 ppm or less that is accompanied by a decrease in the fluorescence intensity of L by about 10-12% (FIG. 5). Comparison of the fluorescence data obtained among all the different solvent systems clearly suggest that while L retained its sensitivity toward $Hg^{2+}$ in all the aqueous acetonitrile solutions, it is highly selective in 50% aqueous solution implying that L can be a selective receptor for $Hg^{2+}$ in aqueous solution.

Example 6

Study of $Hg^{2+}$ Ion Binding with Aminomethyl Benzimidazole Derivative of Calix[4]arene (L) Using Absorption Spectra To confirm the binding of $Hg^{2+}$ with calix[4]arene derivative L, absorption spectral studies were carried out for the titration of $Hg^{2+}$ with L in 1:1 aqueous solution. Calix[4]arene derivative L (0.00303 M) was dissolved in $CH_3CN$, and $Hg(ClO_4)_2$ (0.00303 M) taken in $H_2O:CH_3CN$ (1:1) were used for titrations. Titrations were carried out by varying the equivalents of metal ion between 0 and 4.0 using the additions of 0, 20, 40, 60, 80, 100, 120, 160, 180, 220, 250, 300, 350, and 400 μL stock solution and by fixing the ligand concentration as constant at 100 μL and all the solutions were diluted to 3 mL using $H_2O:CH_3CN$ (1:1) solvent system before used for the study. Same procedure was followed for recording the absorption spectra of the titration of other divalent metal ions $M^{2+}$ with calix[4]arene derivative L.

Figure 6A:
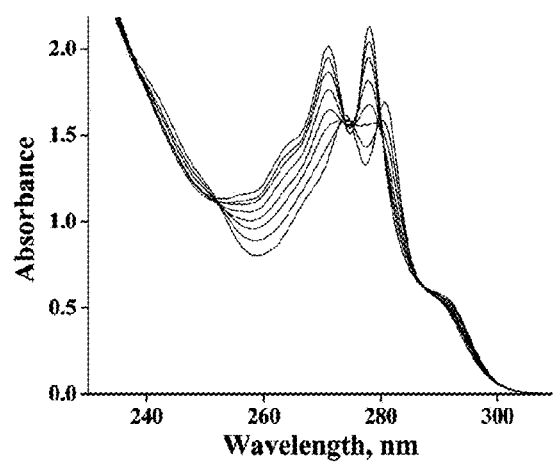
FIG. 6 depicts an illustrative embodiment of an absorption spectral data during the titration of 2-aminomethyl benzimidazole derivative of calix[4]arene (compound L) with $Hg^{2+}$: (a) absorption spectral traces in case of $Hg^{2+}$; (b) absorbance versus $[Hg^{2+}]/[L]$ mol ratio, 271 nm band (○), 277 nm band (■).
Figure 6B:
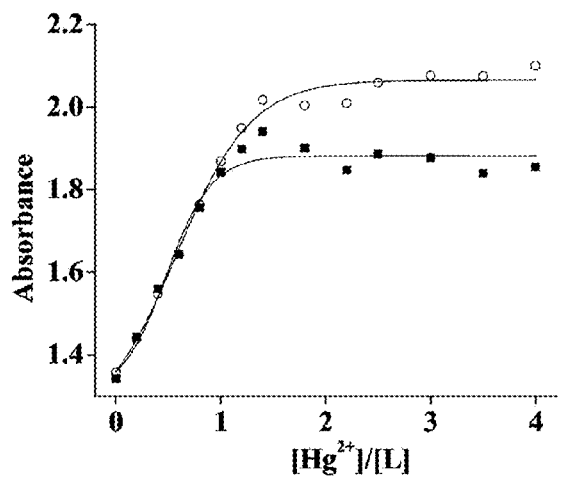
Figure 7:
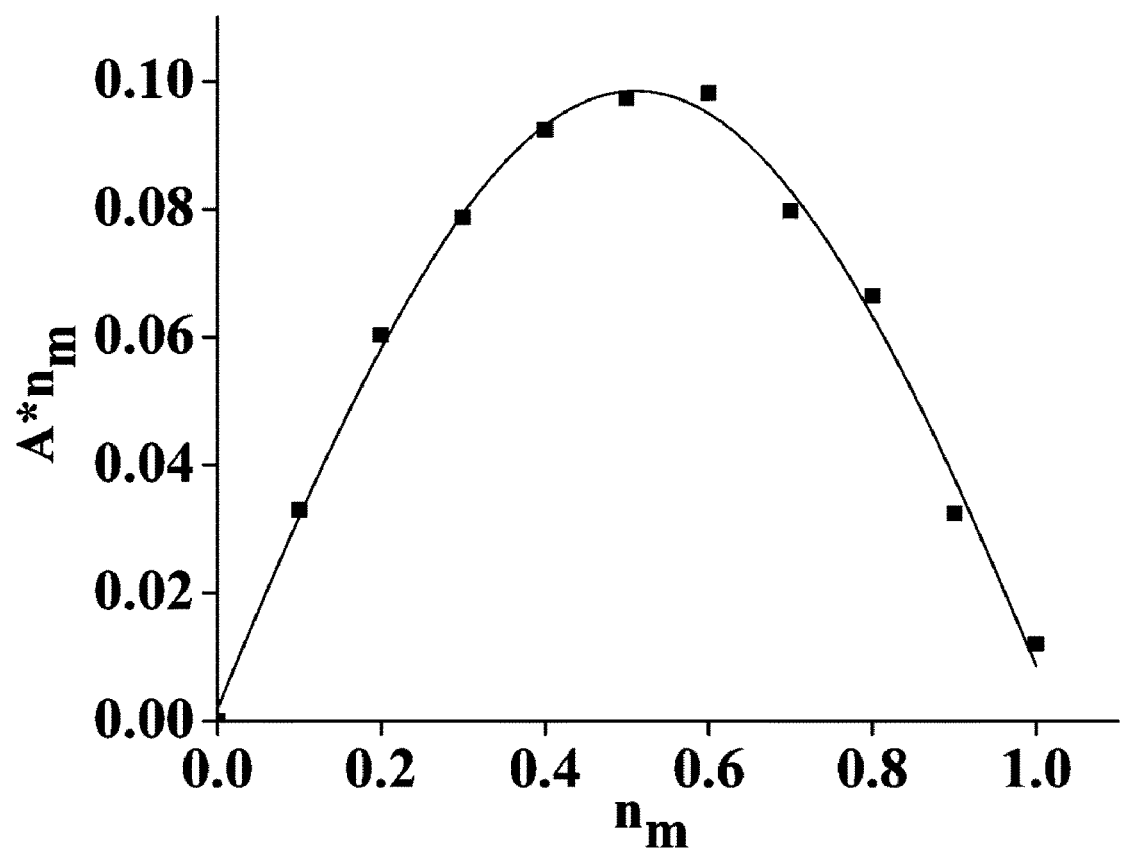
FIG. 7 depicts an illustrative embodiment of a Job plot of $n_m$ versus $A*n_m$, where $n_m$ is mol fraction of the metal ion added and A is absorbance for $Hg^{2+}$

In the case of $Hg^{2+}$, spectral changes and isosbestic points were observed at 252 and 286 nm in the titration, indicating a transition between the free species and the complexed species. Quantitative changes observed in two absorption bands are suggestive of stoichiometric reaction between L and $Hg^{2+}$ (FIGS. 6a-b) and the complexes formed were confirmed to be 1:1 based on Job plots made using the absorption data (FIG. 7).

Example 7

Study of $Hg^{2+}$ Ion Binding with Aminomethyl Benzimidazole Derivative of Calix[4]arene (L) Using ESI MS and NMR In order to confirm the binding and stoichiometry of $Hg^{2+}$ with calix[4]arene derivative L, ESI MS spectra were measured and the formation of 1:1 species was found at m/z 1223.5, where its isotopic peak pattern supports the presence of $Hg^{2+}$.

Calix[4]arene derivative L (0.0245 M) was dissolved in 0.4 mL of DMSO-$d_6$ and the $^1H$ NMR spectra was recorded. Metal ion titrations were carried out by adding different volumes of viz., 10, 20, 30, 40, 60, 80, 120, and 160 μL of bulk $Hg(ClO_4)_2$ (0.245 M) solution to a solution of L to result in $[Hg^{2+}]/[L]$ mole ratio of 0-4.

Figure 8:
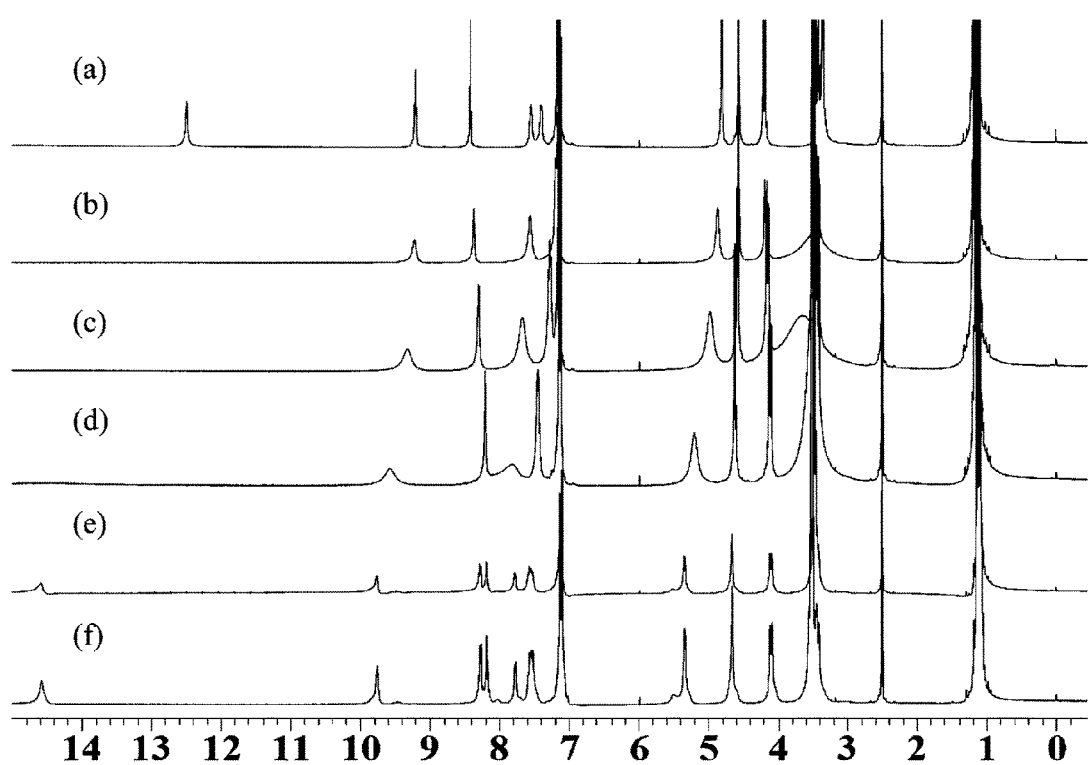
FIG. 8 depicts an illustrative embodiment ¹H NMR spectra measured during the titration of L with $Hg^{2+}$ (in DMSO d6). (a) L, (b) L+0.25 equiv $Hg^{2+}$, (c) L+0.5 equiv $Hg^{2+}$, (d) L+1 equiv $Hg^{2+}$, (e) L+1.5 equiv $Hg^{2+}$, (f) L+2 equiv $Hg^{2+}$.
Figure 9:
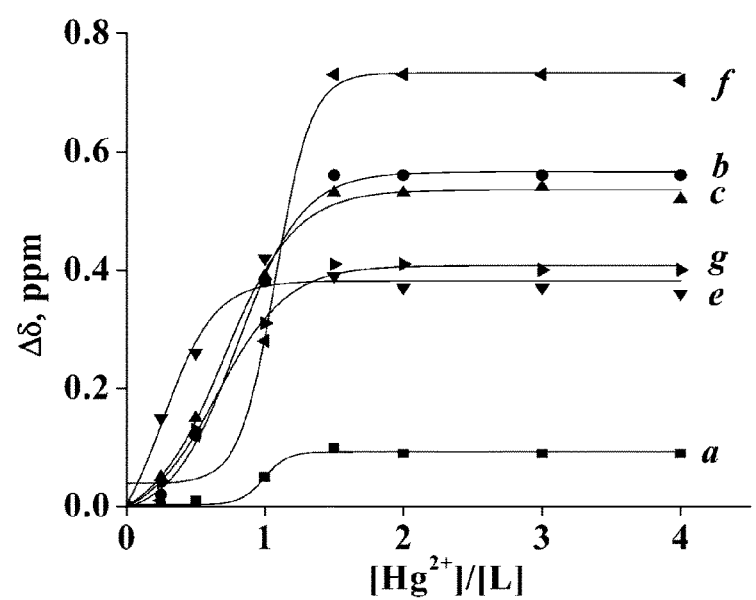
FIG. 9. depicts metal ion-induced downfield shifts $\Delta\delta$ ($\Delta\delta=\delta_{(L+Hg^{2+})}-\delta_L$) observed with different protons of L at various mole ratios of $[Hg^{2+}]/[L]$. The labeling for various protons can be seen from the given structure.
Figure 9:
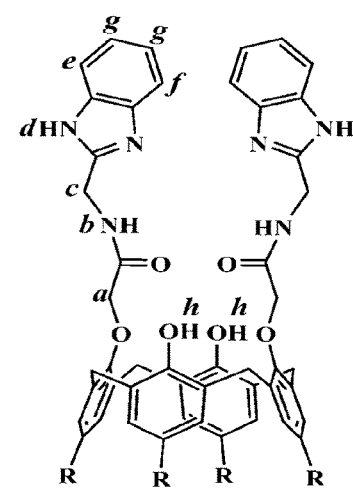

$^1H$ NMR spectra showed marginal to considerable downfield shifts in the δ of C— and N— bound protons of the pendant, amide and benzimidazole moieties to different extents as can be seen from the spectra given in FIG. 8. The N—H protons of the benzimidazole showed a downfield shift of 2.5 ppm and the other benzene protons of the benzimidazole moiety also exhibited large downfield shifts. Corresponding metal ion induced shifts for different protons are plotted in FIG. 9 and the data indicate that the $Hg^{2+}$ ion mainly interacts with the benzimidazole part of the calix[4]arene derivative. $Hg^{2+}$ induced downfield shifts have also been noticed with the benzimidazole carbons in $^{13}C$ NMR spectrum. Thus the NMR study clearly supports the binding of $Hg^{2+}$ to benzimidazole moieties in L.

Example 9

Binding of Other Divalent Ions $M^{2+}$ with Calix[4]arene Derivative L

Similar titrations of calix[4]arene derivative L were carried out with other divalent ions, viz., $Mn^{2+}$, $Fe^{2+}$, $Co^{2+}$, $Ni^{2+}$, $Cu^{2+}$, $Zn^{2+}$, $Cd^{2+}$, $Hg^{2+}$, $Pb^{2+}$, $Ca^{2+}$, and $Mg^{2+}$. The titration of L with $M^{2+}$ in $CH_3CN$ showed fluorescence quenching toward all ions except $Zn^{2+}$, $Ca^{2+}$ and $Mg^{2+}$, wherein the quenching follows a trend, viz., $Cu^{2+}>>Co^{2+}>Hg^{2+}>Mn^{2+}\approx Fe^{2+}\approx Ni^{2+}$. Similar titrations carried out in $CH_3OH$ also exhibited quenching with a number of ions and the trend in the fluorescence quenching has been noted to be $Cu^{2+}Hg^{2+}>Zn^{2+}>Fe^{2+}$. Though L seems to differentiate metal ions better in $CH_3OH$ than in $CH_3CN$, there is still no selectivity in any of these solvents toward any one metal ion because either in $CH_3OH$ or in $CH_3CN$ more than one metal ion shows changes in the fluorescence of L. However, the steady-state fluorescence data obtained from the titration of calix[4]arene derivative L with $M^{2+}$ clearly suggests that calix[4]arene derivative L can selectively detect $Hg^{2+}$ in aqueous-organic solutions such as water-acetonitrile solutions. Various ratios of $H_2O:CH_3CN$ were employed and the sensitivity of $Hg^{2+}$ detection was found to be maximum for 1:1 $H_2O:CH_3CN$ ratio.

Example 10

Competitive Metal Ion Titration Studies of $M^{2+}$ Ion Complex with Aminomethyl Benzimidazole Derivative of Calix[4]arene (L)

In order to establish whether calix[4]arene derivative L can selectively recognize $Hg^{2+}$ even in the presence of other metal ions, two types of competitive metal ion titrations were carried out in 1:1 aqueous solution. While in one, the $Hg^{2+}$ bound L was titrated with the other $M^{2+}$, viz., $\{L+2*Hg^{2+}\}$ by $M^{2+}$, in the second case it was the reverse type of titration, viz., $\{L+5*M^{2+}\}$ by $Hg^{2+}$. Based on the two titrations, it is noticed that no $M^{2+}$ has any effect on the sensitivity of L towards $Hg^{2+}$. Thus, the selectivity towards $Hg^{2+}$ is retained even in the presence of any other metal ions.

Example 11

Fluorescence Life Time Studies of $Hg^{2+}$ Ion Complex with Aminomethyl Benzimidazole Derivative of Calix[4]arene (L)

The formation of the complexed species by calix[4]arene derivative (L) was further studied by measuring the fluorescence life times of the complexes during the titration.

The fluorescence decay data of calix[4]arene derivative (L) (FIG. 9) in 50% aqueous solution can be primarily fitted to a single exponential species (98%) having lifetime of 0.45 ns that is characteristic of the benzimidazole component. Titration of this with 1 equivalent of $Hg^{2+}$ brought significant changes in the fluorescence decay pattern that can be fitted with biexponential yielding two life times, viz., 0.55 and 0.15 ns with species ratio of 25% and 75% respectively. Further, the titration of this mixture with one additional equivalent of $Hg^{2+}$ (a total of 2 equiv of $Hg^{2+}$) did not bring much change in the decay behavior by exhibiting two species with life times of 0.63 and 0.16 ns and a species ratio of 12% and 88% respectively. Thus the lifetime of the major species present in $Hg^{2+}$ bound case results in a decrease by 3-fold. Thus the fluorescence lifetime measurements clearly suggest that the $Hg^{2+}$ ion binds to benzimidazole moieties and thereby demonstrate the advantage of these moieties when connected to the calix[4]arene platform.

Example 12

Figure 10:
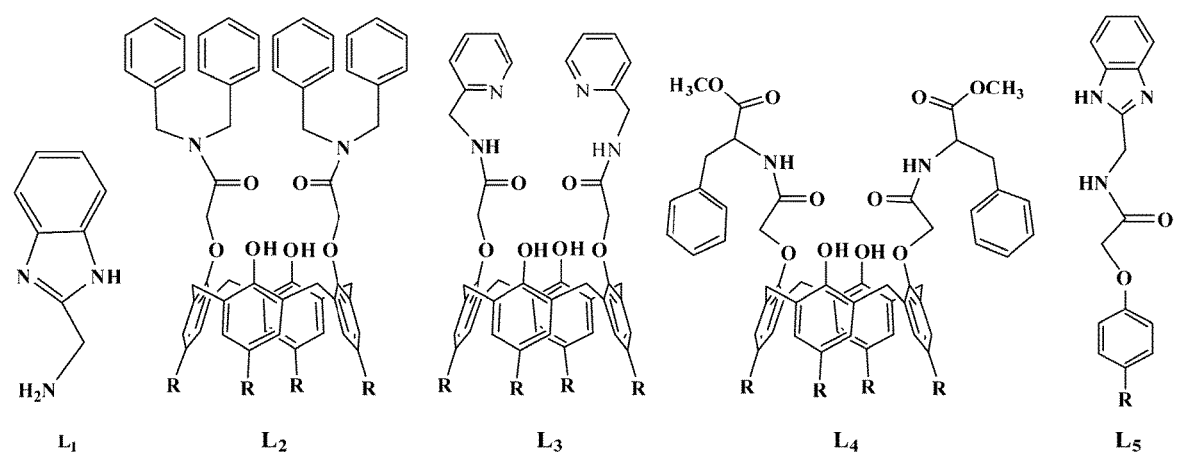
FIG. 10 depicts an illustrative embodiment of schematic structures of the control molecules $L_1$, $L_2$, $L_3$, $L_4$, and $L_5$. R=tert-butyl.

Confirmation of Binding Core of 2-Aminomethyl Benzimidazole Derivative of Calix[4]arene The role of calix[4]arene platform and the benzimidazole moieties in the recognition of $Hg^{2+}$ by L was proven by studying fluorescence properties of the reference molecules (FIG. 10), viz., $L_1, L_2, L_3, L_4$ and $L_5$ with different metal ions. $L_1$ was purchased, $L_2, L_3$, and $L_4$ were synthesized by reacting Compound of Formula IX with the appropriate amine moiety, viz., dibenzylamine, 2-aminomethylpyridine and methyl ester of phenylalanine respectively to result in $L_2, L_3$, and $L_4$. $L_5$ was synthesized starting from p-tert-butyl-phenol followed by ester, then acid and its coupling to give the amide derivative of benzimidazole. All these derivatives were characterized by NMR, FTIR, and mass spectroscopy (see Joseph, R. et al, *J. Org. Chem.* 2008, 73, 5745).

Figure 12A:
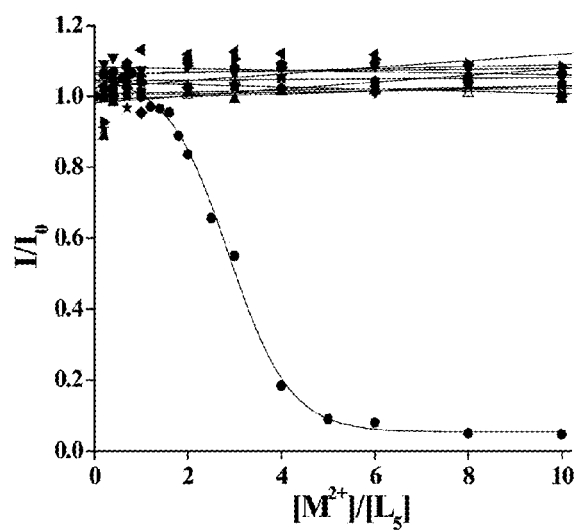
FIG. 12 depicts an illustrative embodiment of plots of $(I/I_o)$ as a function of metal to the ligand mole ratio during the fluorescence titration in aqueous acetonitrile: (a) titration of $L_5$ with $M^{2+}$ (symbols carry same meaning as those given in FIG. 10); (b) titration of L (●) and $L_5$ (○) with $Hg^{2+}$.
Figure 12B:
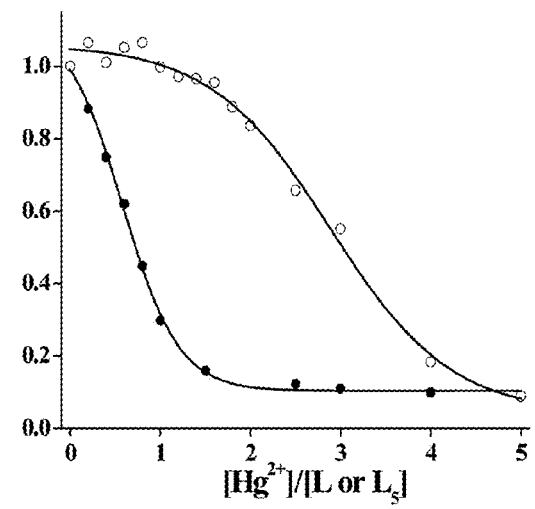

The fluorescence data obtained with $L_1$ clearly indicate that more than one $M^{2+}$ quenches the fluorescence and hence is not selective to any $M^{2+}$. No change in fluorescence is observed in case of the titration of $L_2$ with any $M^{2+}$ and hence, $L_2$ is sensitive to any metal ion. Even $L_3$ does not show any significant changes in the fluorescence by all the $M^{2+}$, except the $Hg^{2+}$, which shows only a partial quenching beyond 10 equivalents and hence does not exhibit much sensitivity toward $Hg^{2+}$. $L_4$ does not show any response to $M^{2+}$ including $Hg^{2+}$ and hence is neither sensitive nor selective in aqueous solution toward any metal ion. Comparison of the fluorescence titration data of $\{L+M^{2+}\}$ with that of $\{L_1+M^{2+}\}$ clearly suggest that the presence of benzimidazole moiety alone, as in $L_1$, is not sufficient enough for the recognition of $Hg^{2+}$ (FIG. 11). Although $L_5$ is sensitive only toward $Hg^{2+}$ among all the different $M^{2+}$ studied, total fluorescence quenching of $L_5$ occurs only beyond four equivalents of $Hg^{2+}$ indicating that the rate of quenching of fluorescence is much slower with $L_5$ as compared to L. Comparison of $I/I_0$ plots of the titration of L and $L_5$ with $Hg^{2+}$ clearly differentiate the species formed in case of $L_5$ from that formed with L besides suggesting the binding of benzimidazole moiety to $Hg^{2+}$ (FIG. 12). Whereas L forms 1:1 species with $Hg^{2+}$, in case of $L_5$, at least two or three molecules are required to form the $Hg^{2+}$ complex. The results obtained from the reference molecules suggest that the receptor molecule, L exhibits more sensitivity and selectivity towards $Hg^{2+}$ by using both its benzimidazole arms simultaneously wherein the calixarene moiety acts as a platform.

Example 13

Computational Calculations

For the computational calculations of the metal ion binding, the crystal structure of the calix[4]arene derivative (L) was used. L was optimized to highest level of HF/6-31G through a cascade process, viz., AM1→HF/STO-3G→HF/3-21G→HF/6-31G. The initial guess for the mercury complex was obtained by taking the optimized structure of L from HF/6-31G and simply placing the $Hg^{2+}$ ion well above the binding core so that there are no interactions present between $Hg^{2+}$ and L. Comparison of the benzimidazole arms in L with those present in the complex suggests that the corresponding dihedral angles have to be changed to bring $N_2$ and $N_5$ in line to form coordination with $Hg^{2+}$ when compared to that present in free L. Since the number of atoms involved in the computations was too large, a model (L') was built by replacing the upper rim t-butyl groups with hydrogens. Thus the computational optimizations were also done with $[HgL]^{2+}$ as well as with $[HgL']^{2+}$. In both the ligands, viz., L and L', the conformations of the arms were found to be similar. Also the geometry about the $Hg^{2+}$ was found to be exactly same in both the complexes, viz., $[HgL]^{2+}$ and $[HgL']^{2+}$. Thus, the L' has the same binding features as those of L.

Gaussian 03, Revision C.02, M. J. Frisch, G. W. Trucks, H. B. Schlegel, G. E. Scuseria, M. A. Robb, J. R. Cheeseman, J. A. Montgomery, Jr., T. Vreven, K. N. Kudin, J. C. Burant, J. M. Millam, S. S. Iyengar, J. Tomasi, V. Barone, B. Mennucci, M. Cossi, G. Scalmani, N. Rega, G. A. Petersson, H. Nakatsuji, M. Hada, M. Ehara, K. Toyota, R. Fukuda, J. Hasegawa, M. Ishida, T. Nakajima, Y. Honda, O. Kitao, H. Nakai, M. Klene, X. Li, J. E. Knox, H. P. Hratchian, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, P. Y. Ayala, K. Morokuma, G. A. Voth, P. Salvador, J. J. Dannenberg, V. G. Zakrzewski, S. Dapprich, A. D. Daniels, M. C. Strain, O. Farkas, D. K. Malick, A. D. Rabuck, K. Raghavachari, J. B. Foresman, J. V. Ortiz, Q. Cui, A. G. Baboul, S. Clifford, J. Cioslowski, B. B. Stefanov, G. Liu, A. Liashenko, P. Piskorz, I. Komaromi, R. L. Martin, D. J. Fox, T. Keith, M. A. Al-Laham, C. Y. Peng, A. Nanayakkara, M. Challacombe, P. M. W. Gill, B. Johnson, W. Chen, M. W. Wong, C. Gonzalez, and J. A. Pople, Gaussian, Inc., Wallingford Conn., 2004.

TABLE 4

Cartesian coordinates of L as obtained from HF/6-31G level of optimization.

| Z | Cartesian coordinates | | | Z | Cartesian coordinates | | |
|---|---|---|---|---|---|---|---|
| | x | y | z | | x | y | z |
| 1 | −6.410131 | −4.829585 | 3.930630 | 1 | 3.056244 | 8.176040 | 1.104662 |
| 1 | −6.889571 | −2.388661 | 4.097993 | 1 | 0.415483 | 2.459854 | 3.875351 |
| 6 | −6.047696 | −4.161571 | 3.151669 | 6 | 1.637441 | 3.927407 | 2.079562 |
| 6 | −6.327695 | −2.763919 | 3.245352 | 6 | 2.699455 | 2.091669 | −3.034817 |
| 1 | −5.094562 | −5.748931 | 1.985371 | 1 | 3.137683 | 3.084305 | −2.996923 |
| 6 | −5.311761 | −4.687338 | 2.070543 | 1 | 1.903484 | 4.092821 | 3.119873 |
| 6 | −5.884781 | −1.853689 | 2.263287 | 6 | 3.083895 | 5.990995 | 1.382947 |
| 1 | −6.090432 | −0.791661 | 2.353633 | 6 | 3.389082 | 6.131324 | 2.904001 |
| 6 | −4.860113 | −3.787692 | 1.076614 | 6 | 0.926814 | −2.608532 | −0.543153 |
| 6 | −5.148569 | −2.386422 | 1.181071 | 1 | 4.045182 | 6.996811 | 3.067512 |
| 7 | −4.113265 | −4.037947 | −0.102827 | 1 | −0.142049 | −3.192510 | 2.005365 |
| 1 | −5.739669 | 0.235133 | −2.943309 | 6 | 1.459347 | −2.760207 | −1.853732 |
| 1 | −7.268993 | 1.640843 | −4.340167 | 6 | 0.627981 | −0.649002 | 2.592431 |
| 7 | −4.565861 | −1.798686 | 0.040116 | 6 | 2.857797 | −0.289715 | −3.447756 |
| 6 | −6.061733 | 1.212991 | −2.601678 | 6 | 1.116848 | 0.611006 | 3.023838 |
| 6 | −6.905599 | 2.023295 | −3.389480 | 6 | 3.476870 | 0.987135 | −3.459708 |
| 1 | −4.556100 | −0.793458 | −0.185583 | 1 | 4.474516 | 1.182934 | −6.070699 |
| 1 | −7.937728 | 3.927736 | −3.610977 | 1 | 3.904396 | 5.245735 | 3.300447 |
| 6 | −3.972100 | −2.835527 | −0.685333 | 1 | 4.867512 | 3.246730 | −4.542560 |
| 6 | −7.283167 | 3.335311 | −2.975244 | 1 | 3.432204 | −1.166840 | −3.736742 |
| 6 | −5.602809 | 1.746340 | −1.375343 | 1 | 4.303264 | 5.759313 | −0.456638 |
| 7 | −4.751814 | 1.169160 | −0.380759 | 6 | 0.952681 | −3.138928 | 1.984528 |
| 8 | −3.677763 | −0.542979 | −3.930187 | 6 | 1.463963 | −3.340778 | 0.548109 |
| 1 | −4.485874 | 1.914552 | 2.706043 | 6 | 4.444514 | 5.810994 | 0.630543 |
| 6 | −5.972770 | 3.069459 | −0.981475 | 6 | 1.435387 | −1.812711 | 2.598861 |
| 6 | −6.818047 | 3.886569 | −1.761886 | 6 | 2.503942 | −3.690709 | −2.051353 |
| 6 | −4.607968 | 2.111206 | 0.560153 | 1 | 2.886963 | −3.812713 | −3.063363 |
| 1 | −3.281305 | 2.996527 | 1.984786 | 6 | 5.103796 | 0.601063 | −5.383710 |
| 1 | −7.099371 | 4.890757 | −1.453285 | 1 | 4.812008 | −0.453246 | −5.471272 |
| 7 | −5.318403 | 3.277266 | 0.250669 | 1 | 5.111581 | 6.658678 | 0.842778 |
| 6 | −3.809299 | 2.038389 | 1.850235 | 6 | 5.456163 | 2.600159 | −3.877380 |
| 1 | −5.356184 | 4.114862 | 0.814715 | 6 | 4.958795 | 1.124588 | −3.915721 |
| 6 | −2.690747 | −0.530480 | −3.125515 | 1 | 2.434368 | 0.651861 | 3.539136 |
| 6 | −3.325004 | −2.663739 | −2.042187 | 1 | 1.320226 | −3.969149 | 2.599723 |
| 1 | −4.091240 | −2.580155 | −2.821654 | 1 | 5.417653 | 3.018326 | −2.862375 |
| 1 | −2.208368 | 1.566260 | −3.132454 | 1 | 2.810413 | 1.614074 | 3.879673 |
| 7 | −2.463865 | −1.467497 | −2.158196 | 1 | 4.947458 | 4.888242 | 0.949754 |
| 1 | −2.744892 | −3.573588 | −2.231861 | 1 | 6.147855 | 0.689632 | −5.715449 |
| 6 | −1.672650 | 0.617863 | −3.258172 | 1 | 6.500858 | 2.642376 | −4.212951 |
| 8 | −3.726354 | 0.099615 | 3.901226 | 6 | 2.520240 | −4.254534 | 0.296982 |
| 1 | −1.235815 | 0.585656 | −4.262784 | 6 | 3.056024 | −4.463462 | −0.995628 |
| 7 | −2.855592 | 0.928091 | 1.899940 | 6 | 2.748165 | −1.713031 | 3.122265 |
| 1 | −0.502212 | 3.009809 | −2.203940 | 1 | 3.393549 | −6.075654 | −3.273980 |
| 1 | −1.629741 | −1.405019 | −1.564730 | 6 | 3.269840 | −0.492847 | 3.615078 |
| 1 | −2.066891 | 0.927901 | 1.247022 | 1 | 5.600874 | −0.785997 | −2.983663 |
| 6 | −2.876765 | 0.051362 | 2.959090 | 6 | 5.874863 | 0.276398 | −2.971219 |
| 1 | 0.843285 | 4.048506 | −2.663820 | 1 | 2.907780 | −4.815716 | 1.142734 |
| 8 | −0.596518 | 0.534609 | −2.244530 | 1 | 5.799666 | 0.630427 | −1.934376 |
| 1 | −0.590305 | 1.228357 | −0.723553 | 1 | 2.820843 | −7.089620 | −1.935693 |
| 6 | 0.576698 | 3.159369 | −2.079285 | 1 | 5.080022 | 1.640734 | 3.350894 |
| 8 | −0.566469 | 1.609497 | 0.201971 | 1 | 3.360250 | −2.609561 | 3.126606 |
| 1 | 1.449347 | 7.476847 | 1.421642 | 6 | 3.689814 | −6.544077 | −2.326671 |
| 6 | 0.904449 | 3.435908 | −0.602597 | 1 | 6.924138 | 0.358280 | −3.288474 |
| 1 | −0.149573 | −1.885144 | −3.012373 | 6 | 4.192491 | −5.485312 | −1.289384 |
| 6 | 0.386704 | 2.618443 | 0.443292 | 1 | 5.187591 | −4.224532 | −2.820174 |
| 6 | 0.767911 | 0.658051 | −2.684844 | 1 | 4.127075 | 1.129038 | 5.744044 |
| 1 | −0.752203 | 1.687981 | 2.807311 | 1 | 5.625684 | 0.302081 | 2.322131 |
| 6 | −1.818972 | −1.066201 | 2.957216 | 6 | 5.538275 | 0.643797 | 3.362140 |
| 6 | 1.348171 | 1.948582 | −2.634244 | 6 | 4.702157 | −0.370406 | 4.212202 |
| 1 | 2.151247 | 5.119839 | −1.072274 | 1 | 4.485153 | −7.271245 | −2.544804 |
| 6 | 1.773627 | 4.498397 | −0.261918 | 1 | 3.829153 | −6.819254 | 0.439612 |
| 1 | −2.298796 | −1.993145 | 2.619629 | 1 | 4.030372 | −0.550467 | 6.309428 |
| 1 | −1.446298 | −1.200562 | 3.977086 | 6 | 5.433357 | −4.735706 | −1.880288 |
| 1 | 2.197742 | 7.297116 | −0.177603 | 1 | 4.609525 | 0.145100 | 5.687277 |
| 6 | 2.402866 | 7.315667 | 0.900591 | 6 | 4.651010 | −6.245008 | −0.009119 |
| 8 | −0.694164 | −0.775356 | 2.034276 | 1 | 6.550556 | 0.742111 | 3.779298 |
| 8 | −0.172961 | −1.742518 | −0.402750 | 1 | 5.052009 | −5.560936 | 0.751354 |
| 6 | 0.773172 | 2.840630 | 1.791527 | 1 | 5.807406 | −3.981953 | −1.174116 |
| 1 | −0.388279 | −1.435174 | 0.523569 | 1 | 6.245409 | −5.447409 | −2.087492 |
| 6 | 0.939876 | −1.919151 | −3.030770 | 1 | 5.593134 | −2.130617 | 3.206762 |

TABLE 4-continued

Cartesian coordinates of L as obtained from HF/6-31G level of optimization.

| Z | Cartesian coordinates | | | Z | Cartesian coordinates | | |
|---|---|---|---|---|---|---|---|
| | x | y | z | | x | y | z |
| 1 | 1.230596 | −2.423707 | −3.962236 | 1 | 4.932983 | −2.486606 | 4.823557 |
| 1 | 2.474949 | 6.292492 | 3.491431 | 6 | 5.457906 | −1.732484 | 4.221477 |
| 6 | 0.305410 | 1.916209 | 2.927160 | 1 | 5.615847 | 0.237548 | 6.119699 |
| 6 | 1.512171 | −0.490178 | −3.058221 | 1 | 5.447678 | −6.954515 | −0.270377 |
| 6 | 2.150596 | 4.783855 | 1.075452 | 1 | 6.455438 | −1.593616 | 4.659202 |

TABLE 5

Cartesian coordinates of L' obtained from HF/6-31G level of optimization.

| Z | Cartesian coordinates | | | Z | Cartesian coordinates | | |
|---|---|---|---|---|---|---|---|
| | x | y | z | | x | y | z |
| 6 | 3.696833 | 3.612334 | 1.407905 | 1 | 0.803926 | 0.878922 | 4.073125 |
| 6 | 4.103915 | 2.294578 | 1.486217 | 8 | 0.055100 | 0.617948 | 2.116914 |
| 7 | 3.117578 | 3.863585 | 0.164217 | 8 | 0.462069 | 1.628622 | 0.326213 |
| 7 | 3.768790 | 1.720683 | 0.267179 | 6 | 1.466090 | 2.920625 | 1.829655 |
| 1 | 3.899767 | 0.730489 | 0.958 | 1 | 0.223891 | 1.334134 | 0.593931 |
| 6 | 3.180903 | 2.702712 | 0.499368 | 6 | 1.546941 | 1.867042 | 2.925950 |
| 6 | 4.454704 | 1.635369 | 1.668803 | 1 | 1.837229 | 2.383622 | 3.848351 |
| 7 | 4.019962 | 1.101110 | 0.450876 | 6 | 0.994250 | 2.024036 | 2.970275 |
| 8 | 3.038305 | 0.394070 | 3.799011 | 6 | 2.135194 | 0.458817 | 2.965461 |
| 1 | 4.023322 | 1.815345 | 2.433270 | 6 | 2.857165 | 4.777246 | 1.067713 |
| 6 | 4.407965 | 3.008237 | 1.613666 | 1 | 1.131725 | 2.573708 | 3.908977 |
| 6 | 3.706863 | 2.136205 | 0.331883 | 6 | 2.351080 | 3.975777 | 2.094200 |
| 1 | 2.847992 | 3.075492 | 2.037484 | 6 | 3.344979 | 2.096221 | 2.957212 |
| 7 | 3.930647 | 3.316779 | 0.341281 | 1 | 3.817207 | 3.073573 | 2.934463 |
| 6 | 3.213017 | 2.081157 | 1.744360 | 1 | 2.644791 | 4.166854 | 3.122429 |
| 1 | 3.767030 | 4.242889 | 0.020302 | 6 | 1.518293 | 2.523101 | 0.450697 |
| 6 | 2.043493 | 0.432839 | 3.027927 | 1 | 0.414238 | 3.028298 | 2.073808 |
| 6 | 2.734923 | 2.515252 | 1.911804 | 6 | 2.045273 | 2.697168 | 1.747464 |
| 1 | 3.579487 | 2.338044 | 2.585847 | 1 | 1.263951 | 0.526221 | 2.651093 |
| 1 | 1.519785 | 1.635727 | 3.074880 | 6 | 3.474837 | 0.285519 | 3.353854 |
| 7 | 1.819790 | 1.376179 | 2.088941 | 6 | 1.775041 | 0.715030 | 3.068494 |
| 1 | 2.245870 | 3.445379 | 2.217209 | 6 | 4.073272 | 0.975518 | 3.362862 |
| 6 | 1.007539 | 0.674074 | 3.178299 | 1 | 4.052021 | 1.159298 | 3.639564 |
| 8 | 3.263502 | 0.062811 | 3.700894 | 6 | 1.508582 | 3.010327 | 2.064413 |
| 1 | 0.568035 | 0.614205 | 4.178409 | 6 | 2.025886 | 3.246144 | 0.648708 |
| 7 | 2.168324 | 1.080521 | 1.938542 | 6 | 2.031022 | 1.705978 | 2.662429 |
| 1 | 0.169668 | 3.035585 | 2.130665 | 6 | 3.065803 | 3.640012 | 1.930892 |
| 1 | 0.985752 | 1.330268 | 1.496703 | 1 | 3.463134 | 3.795176 | 2.937 |
| 1 | 1.332155 | 1.118156 | 1.348358 | 6 | 3.087987 | 0.734651 | 3.568409 |
| 6 | 2.286460 | 0.145891 | 2.915602 | 1 | 1.838053 | 3.844073 | 2.692833 |
| 1 | 1.510854 | 4.060665 | 2.617242 | 1 | 3.507379 | 1.679138 | 3.900808 |
| 8 | 0.063166 | 0.596498 | 2.169989 | 6 | 3.054122 | 4.173235 | 0.420333 |
| 1 | 0.075857 | 1.307645 | 0.638474 | 1 | 3.569965 | 4.382692 | 0.859632 |
| 6 | 1.248626 | 3.181857 | 2.018901 | 6 | 3.337583 | 1.636614 | 3.167017 |
| 8 | 0.112514 | 1.709016 | 0.275227 | 6 | 3.859633 | 0.427179 | 3.630510 |
| 6 | 1.593021 | 3.474821 | 0.561986 | 1 | 3.440305 | 4.743819 | 1.260207 |
| 1 | 0.459179 | 1.820746 | 2.919076 | 1 | 3.946642 | 2.535044 | 3.183010 |
| 6 | 1.070678 | 2.695811 | 0.493293 | 1 | 4.555095 | 1.726481 | 2.282291 |
| 6 | 1.418580 | 0.694073 | 2.601198 | 1 | 3.788729 | 4.389522 | 2.149071 |
| 1 | 0.070272 | 1.820278 | 2.875706 | 1 | 4.660171 | 3.766049 | 2.335063 |
| 6 | 1.171448 | 0.879015 | 3.043543 | 1 | 4.721770 | 0.995967 | 2.492763 |
| 6 | 2.005749 | 1.972155 | 2.561954 | 1 | 3.536505 | 5.592537 | 1.292736 |
| 1 | 2.882549 | 5.120599 | 1.058853 | 1 | 4.869568 | 0.387063 | 4.025320 |
| 6 | 2.485722 | 4.511994 | 0.251168 | 1 | 4.353620 | 5.115145 | 1.021340 |
| 1 | 1.591825 | 1.862742 | 2.809946 | 1 | 5.107898 | 1.082807 | 3.671843 |

The initial geometry for the mercury complex was obtained by taking the optimized structure of L from HF/6-31G and simply placing the Hg$^{2+}$ ion well above the binding core so that there are no interactions present between Hg$^{2+}$ and L. This initial structure for the mercury complex was optimized using DFT computations by going through B3LYP/CEP-31G followed by B3LYP/CEP-121G. The optimization study resulted in the formation of a linearly coordinated species of the type N2..Hg..N5 (178.6° with Hg..N distance of 2.092 Å. Such linear coordination was proposed in case of a tetra-4-picolyl derivative of calix[4]arene in the literature. In addition the structure also reveals weak interaction with the amide carbonyl oxygens where the Hg O distance was found to be 2.7 Å. Weak interactions present between the Hg$^{2+}$ and oxygen have been reported in the literature. Comparison of the benzimidazole arms in L with those present in the complex suggests that the corresponding dihedral angles have to be changed to bring $N_2$ and $N_5$ in line to form coordination with Hg$^{2+}$ when compared to that present in the free ligand. As the computational times involved with L was enormously high, initial calculations were performed using mutilated ligand, L'wherein the L' was generated from L simply by replacing the tertiary butyl groups and the benzene portion of the benzimidazole by hydrogens. Thus the computational optimizations were also done with [HgL]$^{2+}$ as well as with [HgL']$^{2+}$. In both the ligands, viz., L and L', the conformations of the arms were found to be similar. Also the geometry about the Hg$^{2+}$ was found to be exactly same in both the complexes, viz., [HgL]$^{2+}$ and [HgL']$^{2+}$.

Stabilisation Energy Calculation

The stabilization energies were computed using the Formula, $$\Delta E_s = \Delta E_{complex} - (\Delta E_{lig} + \Delta E_M^{2+})$$

where $\Delta E_{complex}$=Energy of the complex i.e., [Hg-L']$^{2+}$ or [Hg-L]$^{2+}$ $\Delta E_{lig}$=Energy of the Ligand as it present in the complex, i.e., L' or L"

$\Delta E_M^{2+}$=Sum of energy of cations in case of bi-metallic complexes, e.g., $E_{Hg}^{2+}$ On the basis of these calculations, gas phase stabilization energies were found to be −355.2 and −393.9 Kcal/mol, respectively, for the complexes [HgL]$^{2+}$ and [HgL']$^{2+}$. Single point energy of these optimized complexes were computed in presence of acetonitrile and water solvent dielectric fields and the corresponding average stabilization energies were computed to be −187.9 and −291.7 kcal/mol for [HgL]$^{2+}$ and [HgL']$^{2+}$, respectively.

EQUIVALENTS

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A compound having Formula I:

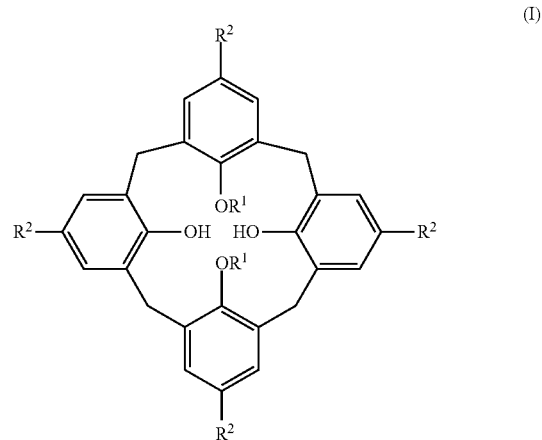

or salts thereof, wherein
each R$^1$ is

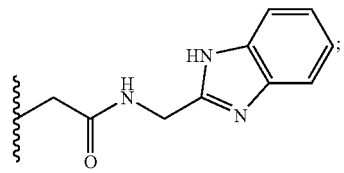

and
each R$^2$ is independently a C$_{3-6}$ straight, branched or cyclic alkyl group.

2. The compound of claim 1 wherein each R$^2$ is a isopropyl, n-butyl, t-butyl, cyclopropyl, cyclobutyl, cyclopentyl or cyclohexyl group.

3. A complex comprising a compound of claim 1 and a Hg$^{2+}$ ion.

4. The compound of claim 1 wherein each R$^2$ is a t-butyl group.

5. A complex comprising a compound of claim 4 and a Hg$^{2+}$ ion.

6. A method of testing for the presence of Hg$^{2+}$ comprising preparing a test sample comprising a compound of claim 4, detecting the fluorescence of the test sample, and comparing the detected fluorescence of the test sample to that of a control sample,
wherein a reduction in fluorescence of the test sample relative to the control sample indicates the presence of Hg$^{2+}$ in the test sample.

7. A method of testing for the presence of Hg$^{2+}$ comprising detecting the fluorescence of a test sample comprising a compound of claim 1, and
comparing the detected fluorescence of the test sample to that of a control sample,
wherein a reduction in fluorescence of the test sample relative to the control sample indicates the presence of Hg$^{2+}$ in the sample.

8. The method of claim 7 wherein the control sample contains substantially the same amount of the compound as the test sample but lacks $Hg^{2+}$.

9. The method of claim 7 wherein the compound is the compound of claim 4.

10. The method of claim 7 wherein the test sample is an aqueous solution.

11. The method of claim 10 wherein the aqueous solution comprises about 40 to about 75% acetonitrile.

12. The method of claim 10 wherein the aqueous solution comprises about 50% acetonitrile.

13. The method of claim 10 wherein the method selectively detects the presence of $Hg^{2+}$ in the presence of one or more different divalent metal ions in the sample.

14. The method of claim 13 wherein the one or more different divalent metal ions are selected from the group consisting of $Ca^{2+}$, $Cd^{2+}$, $Co^{2+}$, $Cu^{2+}$, $Fe^{2+}$, $Mg^{2+}$, $Mn^{2+}$, $Ni^{2+}$, $Pb^{2+}$, and $Zn^{2+}$.

15. A method for preparing a compound of claim 1 comprising contacting 2-aminomethyl benzimidazole in the presence of a suitable base with a compound of Formula II:

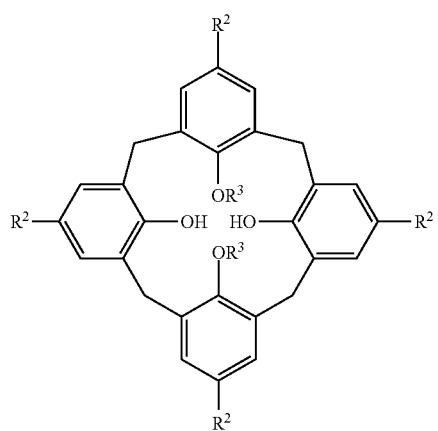

(II)

wherein $R^3$ is —$CH_2COX$ and X is a halide.

16. The method of claim 15 wherein the suitable base is a tertiary amine or a pyridine compound.

17. The method of claim 15 wherein the suitable base is selected from the group consisting of triethylamine, diisopropylethylamine, pyridine, and dimethylaminopyridine.

18. A method for preparing a compound of claim 1 comprising activating carboxyl groups of Formula II for amide bond formation and reacting the activated compound of Formula II with 2-aminomethyl benzimidazole to give the compound of claim 1, wherein the compound of Formula II is:

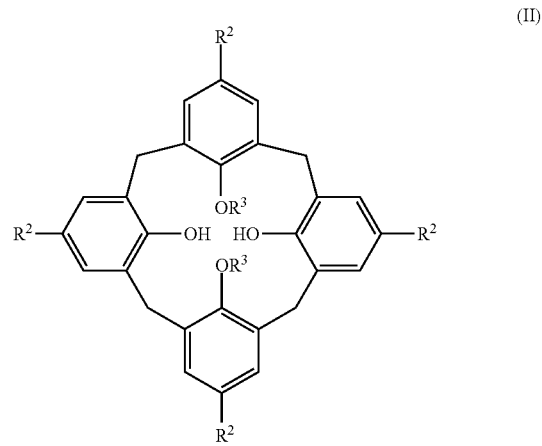

(II)

wherein $R^3$ is —$CH_2COOH$.

19. The method of claim 18 wherein the compound of Formula II is activated by forming an halide from each $R^3$ group.

20. The method of claim 18 wherein the compound of Formula II is activated by forming an active ester, a mixed anhydride or by use of a peptide coupling reagent.

* * * * *

UNITED STATES PATENT AND TRADEMARK OFFICE
CERTIFICATE OF CORRECTION

| | |
|---|---|
| PATENT NO. | : 8,034,622 B2 |
| APPLICATION NO. | : 12/623956 |
| DATED | : October 11, 2011 |
| INVENTOR(S) | : Rao et al. |

It is certified that error appears in the above-identified patent and that said Letters Patent is hereby corrected as shown below:

In Column 2, Line 15, delete "$C^{3-6}$" and insert -- $C_{3-6}$ --, therefor.

In Column 4, Line 36, delete "$Hg^{2+}$" and insert -- $Hg^{2+}$. --, therefor.

In Column 12, Line 1, delete "areas" and insert -- are as --, therefor.

In Column 15, Line 43, delete "HOAt" and insert -- HOAt. --, therefor.

In Column 16, Line 43, delete "(TCSPC)" and insert -- (TRSPC) --, therefor.

In Column 19, Lines 58-59, delete "C, 67.58; H, 7.50; N," and insert -- C 67.58, H 7.50, N --, therefor.

In Column 19, Lines 59-60, delete "C, 67.11; H, 7.11; N," and insert -- C 67.11, H 7.11, N --, therefor.

In Column 21, Line 62, delete "1.390 (8" and insert -- 1.390 (8) --, therefor.

In Column 24, Lines 19-20, delete "C, 53.02; H, 6.41; N," and insert -- C 53.02, H 6.41, N --, therefor.

In Column 24, Line 21, delete "C, 53.41; H, 6.10; N," and insert -- C 53.41, H 6.10, N --, therefor.

In Column 26, Line 42, delete "Example 9" and insert -- Example 8 --, therefor.

In Column 27, Line 1, delete "Example 10" and insert -- Example 9 --, therefor.

In Column 27, Line 18, delete "Example 11" and insert -- Example 10 --, therefor.

In Column 27, Line 46, delete "Example 12" and insert -- Example 11 --, therefor.

In Column 28, Line 25, delete "Example 13" and insert -- Example 12 --, therefor.

In Column 33, Line 4, delete "L'wherein" and insert -- L' wherein --, therefor.

Signed and Sealed this
Fourteenth Day of August, 2012

David J. Kappos
*Director of the United States Patent and Trademark Office*